(12) United States Patent
Lee

(10) Patent No.: US 9,814,671 B2
(45) Date of Patent: Nov. 14, 2017

(54) DRUG DELIVERY DEVICES AND METHODS FOR DRUG DELIVERY

(71) Applicant: TARIS Biomedical LLC, Lexington, MA (US)

(72) Inventor: Heejin Lee, Bedford, MA (US)

(73) Assignee: TARIS Biomedical LLC, Lexington, MA (US)

( * ) Notice: Subject to any disclaimer, the term of this patent is extended or adjusted under 35 U.S.C. 154(b) by 212 days.

(21) Appl. No.: 14/770,494

(22) PCT Filed: Mar. 14, 2014

(86) PCT No.: PCT/US2014/028317
§ 371 (c)(1),
(2) Date: Aug. 26, 2015

(87) PCT Pub. No.: WO2014/144066
PCT Pub. Date: Sep. 18, 2014

(65) Prior Publication Data
US 2016/0008271 A1    Jan. 14, 2016

Related U.S. Application Data

(60) Provisional application No. 61/794,677, filed on Mar. 15, 2013.

(51) Int. Cl.
*A61K 9/00* (2006.01)
*A61K 31/167* (2006.01)
*A61M 31/00* (2006.01)

(52) U.S. Cl.
CPC .......... *A61K 9/0004* (2013.01); *A61K 9/0034* (2013.01); *A61K 31/167* (2013.01); *A61M 31/00* (2013.01)

(58) Field of Classification Search
CPC ... A61K 9/0034; A61K 9/0004; A61M 31/00; A61M 31/002; A61M 2210/1085; A61M 2205/0216
See application file for complete search history.

(56) References Cited

U.S. PATENT DOCUMENTS 4,657,536 A    4/1987  Dorman
5,221,278 A *  6/1993  Linkwitz .............. A61K 9/0004
                                             424/457

(Continued)

FOREIGN PATENT DOCUMENTS

WO    2015026813 A1    2/2015

*Primary Examiner* — Kevin C Sirmons
*Assistant Examiner* — William Carpenter
(74) *Attorney, Agent, or Firm* — Eversheds Sutherland (US) LLP

(57) ABSTRACT

An orifice-free drug delivery device is provided. In an embodiment, the device includes a body having at least one water-permeable wall bounding a reservoir defined within the body. A drug formulation is disposed within the reservoir. The body has an elastic portion and at least one restraining plug closing off an opening of the body. The opening is in fluid communication with the reservoir, and the restraining plug contacts the elastic portion of the body and controls release of the drug from the device by the transient formation of one or more microchannels between the elastic portion of the body and the at least one restraining plug. The elastic portion may define an opening having an inner diameter, which is exceeded by the outer diameter of the restraining plug by at least 3%.

22 Claims, 16 Drawing Sheets

(56) References Cited

U.S. PATENT DOCUMENTS

| | | | |
|---|---|---|---|
| 5,340,590 A * | 8/1994 | Wong | A61K 9/0004 424/472 |
| 5,456,679 A * | 10/1995 | Balaban | A61K 9/0004 424/422 |
| 5,681,584 A | 10/1997 | Savastano et al. | |
| 5,997,527 A * | 12/1999 | Gumucio | A61K 9/0004 424/424 |
| 6,217,906 B1 | 4/2001 | Gumucio et al. | |
| 7,207,982 B2 * | 4/2007 | Dionne | A61K 9/0004 424/422 |
| 7,241,457 B2 | 7/2007 | Chen et al. | |
| 8,167,836 B2 | 5/2012 | Lee et al. | |
| 8,343,516 B2 | 1/2013 | Daniel et al. | |
| 8,679,094 B2 | 3/2014 | Cima et al. | |
| 8,801,694 B2 | 8/2014 | Lee et al. | |
| 9,017,312 B2 | 4/2015 | Lee et al. | |
| 2009/0149833 A1 | 6/2009 | Cima et al. | |
| 2010/0003297 A1 | 1/2010 | Tobias et al. | |
| 2010/0330149 A1* | 12/2010 | Daniel | A61K 9/0034 424/430 |
| 2010/0331770 A1 | 12/2010 | Lee et al. | |
| 2011/0060309 A1* | 3/2011 | Lee | A61K 9/0034 604/500 |
| 2011/0152839 A1* | 6/2011 | Cima | A61K 31/00 604/517 |
| 2011/0166554 A1 | 7/2011 | Alessi et al. | |
| 2012/0089122 A1* | 4/2012 | Lee | A61K 9/0039 604/517 |
| 2012/0203203 A1 | 8/2012 | Lee et al. | |
| 2013/0158675 A1 | 6/2013 | Hutchins, III et al. | |
| 2014/0276637 A1 | 9/2014 | Lee et al. | |

\* cited by examiner

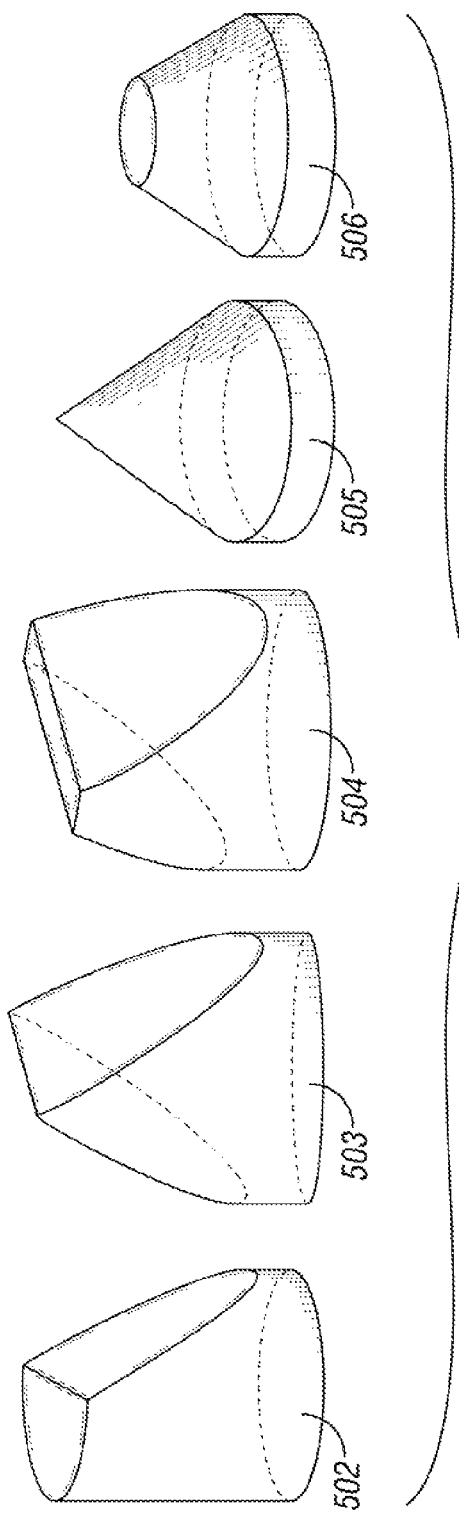
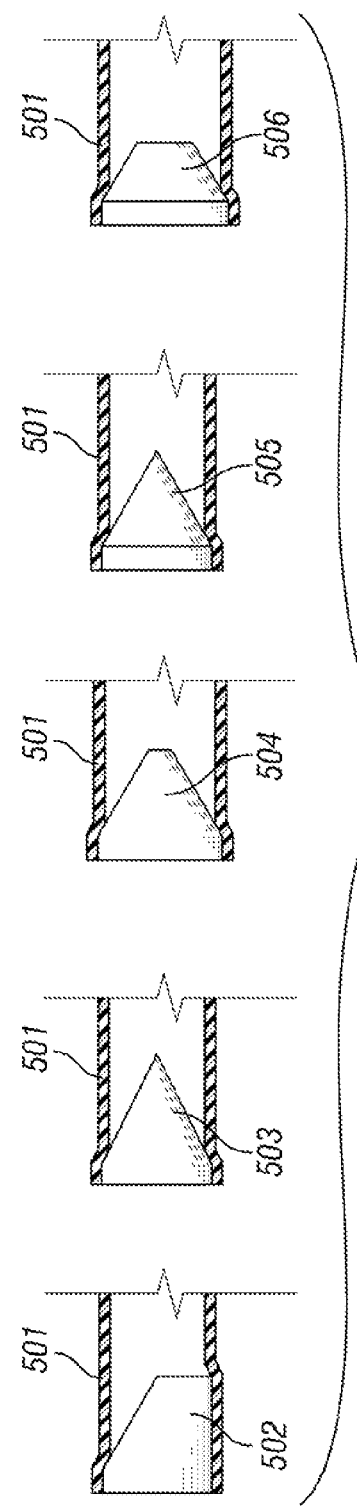
FIG. 6
FIG. 7

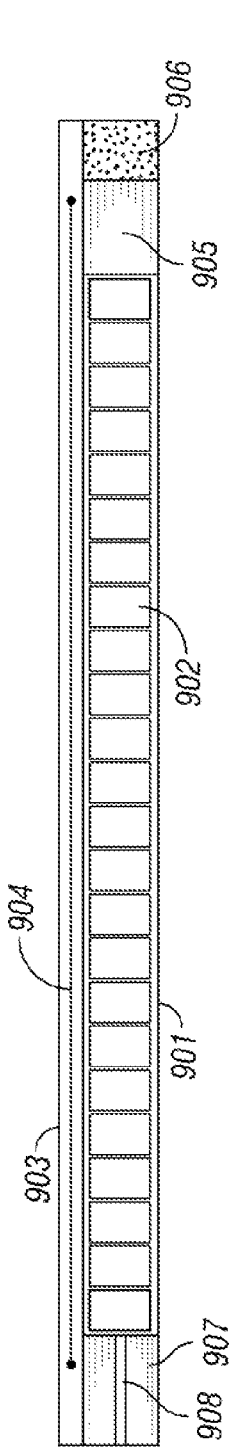
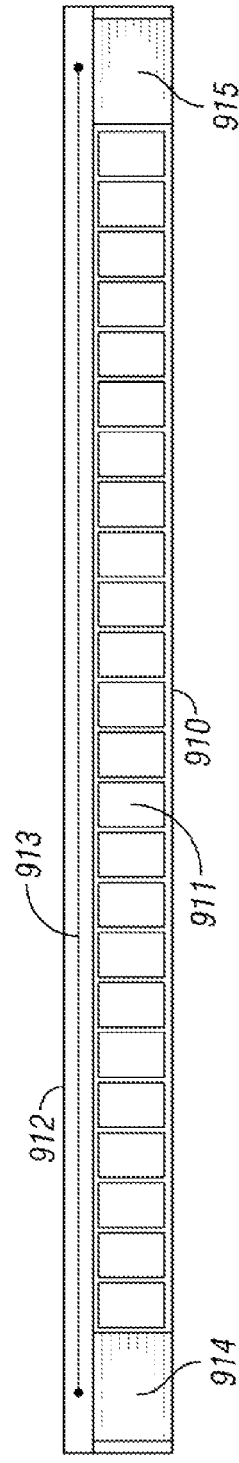
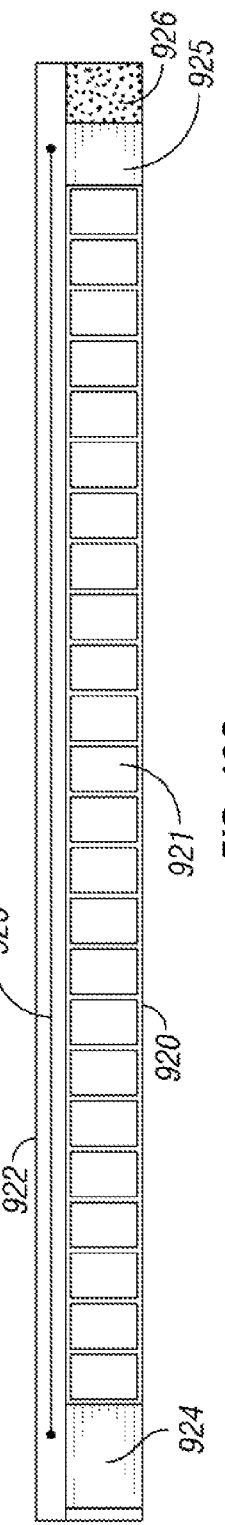
FIG. 10A
FIG. 10B
FIG. 10C

DRUG DELIVERY DEVICES AND METHODS FOR DRUG DELIVERY

CROSS-REFERENCE TO RELATED APPLICATION

This application is a National Stage Entry of PCT/US2014/028317, filed on 14 Mar. 2014, published as WO 2014/144066 on 18 Sep. 2014, and claims priority to and benefit of U.S. Provisional Patent Application No. 61/794,677, filed Mar. 15, 2013, which is incorporated herein by reference.

BACKGROUND

This disclosure generally relates to implantable devices for controlled drug delivery without a pre-defined orifice.

Many current drug delivery devices rely on at least one orifice to permit the release of drugs from the devices. While an orifice may allow for some control over drug release, orifice-containing devices may potentially expel an undesirable amount of drug when compressed after deployment. For example, an orifice-containing device deployed in the bladder may be compressed during bladder contraction, thereby forcing an undesirable amount of drug out of the orifice. The compression of orifice-containing devices may release toxic amounts of drugs, especially when the drugs are potent, such as anti-cancer drugs.

This problem can be mitigated, to some degree, by decreasing the size of the orifice of a particular device. As the size of the orifice decreases, however, the likelihood that the orifice will clog after deployment increases. A clogged orifice is undesirable because it often leads to less reproducible drug release, or it may prevent drug release entirely.

Aside from possible mechanical difficulties, adding an orifice to a device increases the device's complexity and cost of the components and/or manufacturing. This is especially true when an orifice of a small and precise diameter, such as one ranging from 75 to 300 microns, is needed to ensure that the device is capable of releasing drug at a desired rate.

In other cases, a drug delivery device may not have a release orifice and release of drug is controlled by diffusion from a matrix material and/or through a wall. Such configurations which rely on diffusion, however, may limit the drug release kinetics that can be achieved and/or may limit the range of suitable materials of construction to ones that lack the desired biocompatibility, stability, sterilizability, and mechanical properties, including manufacturability, wall thickness, flexibility, etc.

There exists a need for a drug delivery device that overcomes one or more of these disadvantages.

BRIEF SUMMARY

Orifice-free drug delivery devices are provided. In one aspect, a drug delivery device is provided that includes: a body having at least one water-permeable wall bounding a reservoir defined within the body, wherein the body comprises an elastic portion; a drug formulation which comprises a drug, the drug formulation being disposed within the reservoir; and at least one restraining plug closing off an opening of the body, the opening being in fluid communication with the reservoir, wherein the at least one restraining plug contacts the elastic portion of the body and controls release of the drug from the device by the transient formation of one or more microchannels between the elastic portion of the body and the at least one restraining plug. In one embodiment, the device includes a restraining plug having an outer diameter, and the elastic portion of the body defines an opening having an inner diameter, wherein the outer diameter of the restraining plug exceeds the inner diameter of the elastic portion of the body by at least 3%, for example, from 5% to 25%.

In one embodiment, the device is elastically deformable between a relatively straightened shape suitable for insertion through a lumen into a body cavity of a patient and a retention shape suited to retain the device within the body cavity. In a preferred embodiment, the lumen may be the urethra and the body cavity may be the bladder.

Methods of administering a drug to a patient also are provided. In one embodiment, the method includes inserting the drug delivery device of claim 1 into a lumen or body cavity of a patient; and permitting water influx into the reservoir to develop a hydrostatic pressure in the reservoir effective to form one or more microchannels between the elastic portion of the body and the at least one restraining plug, thereby causing the drug to flow from the reservoir, through the microchannels, and out of the device and into the lumen or body cavity of the patient. In one embodiment, the drug is initially is a solid form, and following insertion into the body, the water that enters the reservoir of the device, contacts and solubilizes the drug, and thereafter the dissolved drug exits the device via the microchannels. For example, the drug may be solubilized upon contact with urine when the device is deployed in the bladder.

BRIEF DESCRIPTION OF THE DRAWINGS

FIG. 6 is a perspective view of five different shapes of restraining plugs.

FIG. 7 is a cross-sectional view of the restraining plugs of FIG. 6 as inserted into an elastic portion of the body of a drug delivery device. Only a portion of the body is shown.

FIGS. 10A-10C are cross-sectional views depicting three types of drug delivery devices subjected to testing, including an embodiment of the drug delivery devices described herein.

DETAILED DESCRIPTION

It has been discovered that controlled release of drug can be achieved with the transient formation of microchannels through which a fluidized drug can be dispensed from a delivery device. The microchannels form at an interface of device components in response to a hydrostatic pressure developed in a drug reservoir. Drug delivery devices configured to induce and utilize such microchannels have been developed, which avoid the potential problems associated with conventional devices that require a preformed orifice, including precision miniature orifices that may increase component cost and the risk of clogging, or that are limited by diffusion through or from another material.

In embodiments, the drug delivery device includes a device body having at least one water-permeable wall bounding a drug reservoir defined within the body. A drug formulation which comprises a drug is loaded into the defined drug reservoir. The body includes an elastic portion and has an opening in fluid communication with the drug reservoir. The device further includes a restraining plug closing off the opening, such that the restraining plug contacts the elastic portion of the body and controls release of the drug from the device by the transient formation of one or more microchannels between the elastic portion of the body and the at least one restraining plug.

The term "microchannels," as used herein, refers to a passageway or system of passageways through which drugs can exit the devices described herein. In embodiments, the microchannels form in response to hydrostatic pressure that accumulates in the water-permeable body due to osmotically driven water influx; when the hydrostatic pressure increases above a certain threshold, the microchannels form, thereby forcing at least a portion of drug out of the device and relieving the hydrostatic pressure accumulation in the drug reservoir. The microchannel may collapse at least partially as the hydrostatic pressure has been relieved. This process repeats itself until all or a substantial portion of the drug has been released, or the osmotically driven water influx is insufficient to continue the process.

The microchannels may form anywhere along the inner surface of the elastic portion of the water-permeable body, thereby significantly and beneficially reducing the likelihood of complete clogging—even when insoluble excipients are used in the drug formulation. Advantageously, the microchannels, unlike an orifice, may reduce or eliminate the potential risk of sudden drug discharge when the device is compressed or deformed. For example, when the drug delivery devices are surrounded by body fluid and disposed in an environment that exposes the devices to moderate external mechanical stress, drugs are less likely to be discharged through the microchannels.

Figure 1A:
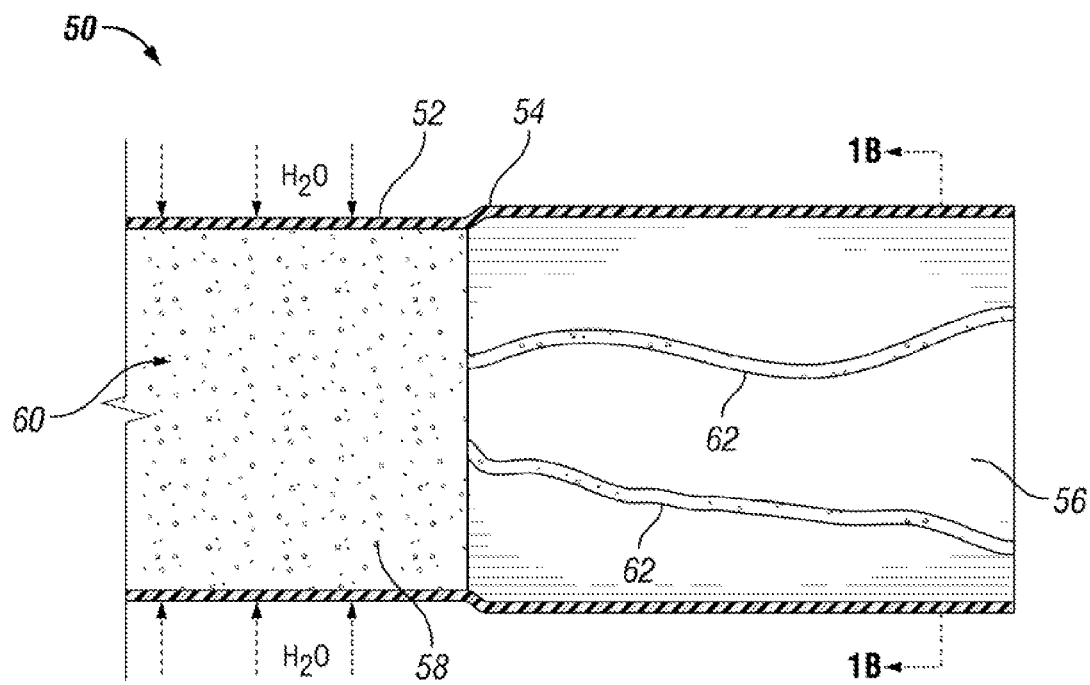
FIGS. 1A-1B are plan and cross-sectional views, respectively, showing part of a drug delivery device in which microchannels are formed to permit release of drug.
Figure 1B:
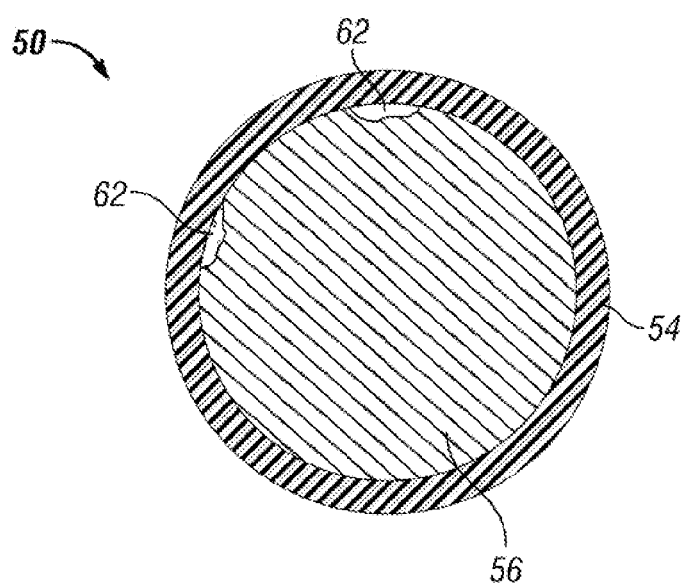

FIGS. 1A and 1B show one embodiment of the microchannels in a drug delivery device. Device 50 includes a body, or housing, 52 having an elastic portion 54 with a restraining plug 56 inserted into an opening in the body 52 such that the elastic portion 54 is positioned against (around) an outer surface of the restraining plug 56. As shown, water diffuses through a water permeable wall of the body 52 and enters the drug reservoir 60, forming fluidized drug 58, which for example may be an aqueous solution comprising the drug initially loaded in the reservoir 60. Hydrostatic pressure in the reservoir 60 causes the fluidized drug to be pushed out of the reservoir between the elastic portion and the restraining plug, through microchannels 62 that are formed therebetween, for example by elastic deformation of one or both of the interfacing surfaces.

The devices, systems, and methods disclosed herein, build upon some features and aspects of the devices, systems and methods described in the following patent application publications: US 2012/0203203 (Lee et al.); US 2012/0089122 (Lee et al.); US 2012/0089121 (Lee et al.); US 2011/0218488 (Boyko et al.); US 2011/0202036 (Boyko et al.); US 2011/0152839 (Cima et al.); US 2011/0060309 (Lee et al.); US 2010/0331770 (Lee et al.); US 2010/0330149 (Daniel et al.); US 2010/0003297 (Tobias et al.); US 2009/0149833 (Cima et al.); and US 2007/0202151 (Lee et al.), which in pertinent part are incorporated by reference herein.

I. The Drug Delivery Device

Figure 2:
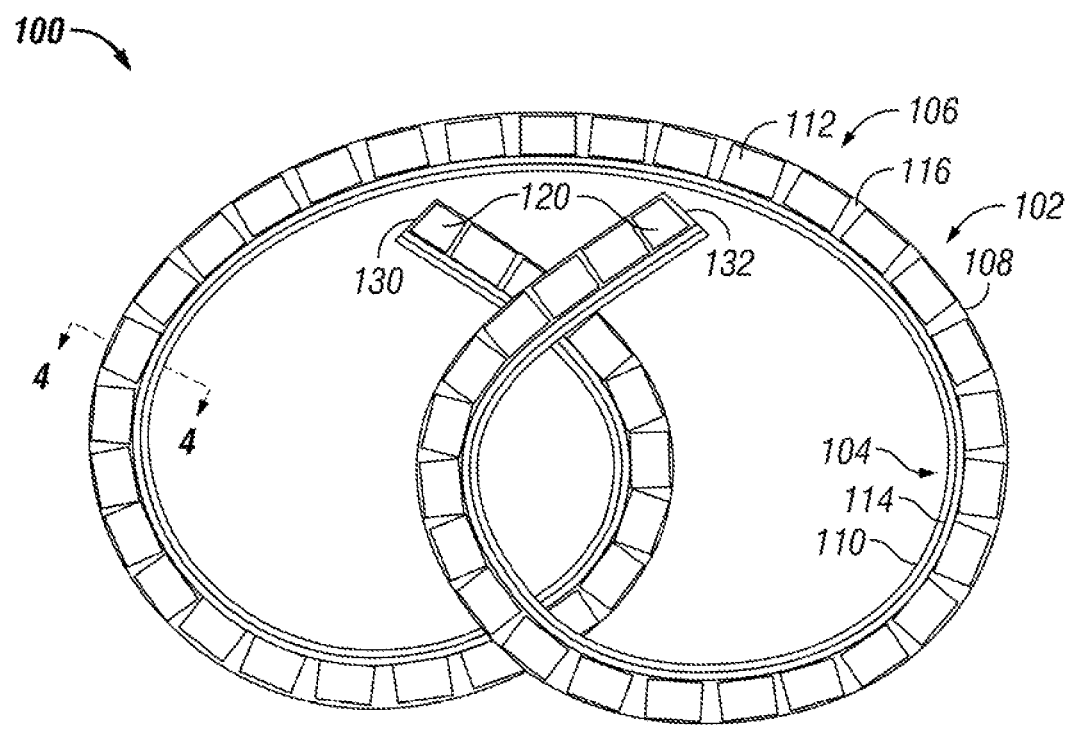
FIG. 2 is a plan view of an embodiment of a drug delivery device.

An embodiment of a drug delivery device 100 is illustrated in FIG. 2. The device 100 includes a water-permeable body having a drug reservoir portion 102 and a retention frame portion 104. In FIG. 2, the device 100 is shown in a relatively expanded shape suited for retention in the body, and in FIG. 3 the device 100 is shown in a relatively lower-profile shape for deployment through the channel 200 of a deployment instrument, such as a cystoscope or other catheter. Following deployment into the body, the device 100 may assume the relatively expanded shape to retain the drug delivery device in the body cavity or lumen.

For the purposes of this disclosure, terms such as "relatively expanded shape", "relatively higher-profile shape", or "retention shape" generally denote any shape suited for retaining the device in the intended deployment location, including but not limited to the pretzel shape shown in FIG. 2 that is suited for retaining the device in the bladder. Similarly, terms such as "relatively lower-profile shape" or "deployment shape" generally denote any shape suited for deploying the drug delivery device into the body, including the linear or elongated shape shown in FIG. 3 that is suited for deploying the device through the working channel of a catheter, cystoscope, or other deployment instrument positioned in a lumen of the body, such as the urethra. In embodiments, the drug delivery device may naturally assume the relatively expanded shape and may be deformed, either manually or with the aid of an external apparatus, into the relatively lower-profile shape for insertion into the body.

Once deployed the device may spontaneously or naturally return to the initial, relatively expanded shape for retention in the body.

In the illustrated embodiment, the drug reservoir and retention frame portions 102, 104 of the drug delivery device 100 are longitudinally aligned and are coupled to each other along their length, although other configurations are possible. For example, the drug reservoir portion 102 may be attached to the retention frame portion 104 at discrete points but otherwise may be separate or spaced apart from the retention frame portion 104.

The drug delivery device 100 includes an elastic or flexible device body 106 that defines a drug reservoir lumen 108 and a retention frame lumen 110. The drug reservoir lumen 108 is designed to house a drug formulation, such as a number of solid drug tablets 112, to form the drug reservoir portion 102. The retention frame lumen 110 is designed to house a retention frame 114 to form the retention frame portion 104. The illustrated lumens 108, 110 are discrete from each other, although other configurations are possible.

Figure 4:
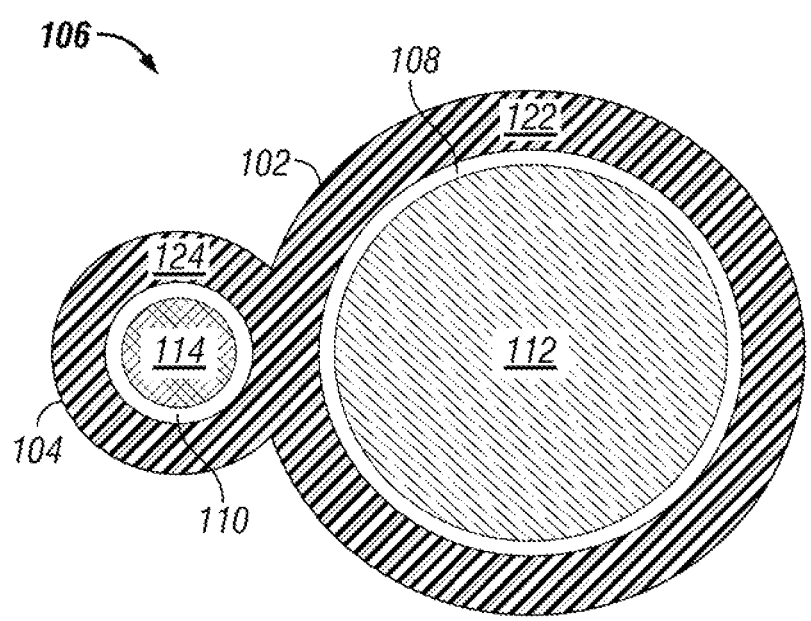
FIG. 4 is a cross-sectional view of the drug delivery device depicted in FIG. 1 along line 4-4.

As shown in the cross-sectional view of FIG. 4, the device body 106 includes a tube or wall 122 that defines the drug reservoir lumen 108 and a tube or wall 124 that defines the retention frame lumen 110. The tubes 122, 124 and lumens 108, 110 can be substantially cylindrical, with the drug reservoir lumen 108 having a relatively larger diameter than the retention frame lumen 110, although other configurations can be selected based on, for example, the amount of drug to be delivered, the diameter of the retention frame, and deployment considerations such as the inner diameter of the deployment instrument. The device body 106 may be formed integrally, such as via molding or extrusion, although separate construction and assembly of the tubes 122, 124 is possible. The wall 124 that defines the retention frame lumen 110 may extend along the entire length of the wall 122 that defines the drug reservoir lumen 108, so that the retention frame lumen 110 has the same length as the drug reservoir lumen 108 as shown, although one wall may be shorter than the other wall in other embodiments. Further, the two walls 122, 124 are attached along the entire length of the device in the illustrated embodiment, although intermittent attachment can be employed. In one example, the wall 122 of the drug reservoir lumen 108 has an inner diameter of about 1.5 mm and an outer diameter of about 1.9 mm, while the wall 124 of the retention frame lumen 110 has an inner diameter of about 0.5 mm and an outer diameter of about 0.9 mm. In another example, the wall 122 of the drug reservoir lumen 108 has an inner diameter of about 2.16 mm and an outer diameter of about 2.56 mm. However, the inner and outer diameters of the wall 122 of the drug reservoir lumen 108 and the wall 124 of the retention frame lumen 110 may be any suitable diameter. The cross-sectional area of the entire body of the device 106 may be about 0.035 $cm^2$ or less. However, the cross-sectional area of the entire body of the device 106 may be any suitable dimension.

As shown in FIG. 2, the drug reservoir lumen 108 is loaded with a number of drug units 112 in a serial arrangement. For example, between about 10 and about 100 drug units 112 may be loaded, such as between about 30 and about 70 drug units 112, or more particularly between about 50 and 60 drug units 112. However, essentially any number of drug units may be used, depending upon the sizes of the reservoir and the drug units. The drug reservoir lumen 108 includes openings 130 and 132, which are shown in this particular embodiment as relatively circular openings at opposite ends of the drug reservoir lumen 108. These openings provide ingress for the drug units 112 to be placed into the drug reservoir lumen 108 during device loading and assembly.

Once the drug units 112 are loaded, restraining plugs 120, as described herein, are disposed in the openings 130 and 132. In one embodiment, only one of the openings has a restraining plug, and the opposed opening is sealed with a plug or other material that does not permit the formation of microchannels. The restraining plugs 120, in this embodiment, are substantially cylindrical plugs inserted into openings 130 and 132. In some instances, each of the restraining plugs 120 may, as described herein, have an outer diameter that is larger than the inner diameter of the drug reservoir lumen 108. In other embodiments, the restraining plugs 120 may be secured within the drug reservoir lumen 108 by an adhesive, but without sealing the lumen. In still other embodiments, the restraining plugs 120 may be secured within the drug reservoir lumen 108 by an external clamp disposed about the drug reservoir lumen 108. The restraining plugs 120 may be secured within the drug reservoir lumen 108 by any means disclosed herein or a combination thereof, as long as it permits the formation of microchannels.

In certain embodiments, each of the restraining plugs 120 may include a cavity for receiving an end portion of the retention frame 114. In some cases, a number of restraining plugs 120 can be positioned in the openings 130 and 132. The restraining plugs 120 may be silicone plugs, ethylene vinyl acetate plugs, or a combination thereof. In embodiments where one of the restraining plugs 120 is omitted, the opening 130 or 132 without the restraining plug 120 is closed with any other suitable biocompatible material. In one example, the material is an adhesive substance that is placed in the drug reservoir lumen 108 in workable form and cures therein. In some embodiments, a restraining plug is inserted into an opening 130 of the drug reservoir lumen, and the other opening 132 of the drug reservoir lumen is sealed with an adhesive.

The retention frame lumen 110 is loaded with the retention frame 114, which may be an elastic wire. The retention frame 110 may be configured to return spontaneously to a retention shape, such as the illustrated example "pretzel" shape or another coiled shape, such as those disclosed in the applications previously incorporated. In particular, the retention frame 114 may retain the device 100 in the body, such as in the bladder. For example, the retention frame 114 may have an elastic limit and modulus that allows the device 100 to be introduced into the body in a relatively lower-profile shape, permits the device 100 to return to the relatively expanded shape once inside the body, and impedes the device from assuming the relatively lower-profile shape within the body in response to expected forces, such as the hydrodynamic forces associated with contraction of the detrusor muscle and urination. Thus, the device 100 may be retained in the body once deployed, limiting or prevent accidental expulsion.

The material used to form the device body 106, at least in part, may be elastic or flexible to permit moving the device 100 between deployment and retention shapes. When the device is in the retention shape, the retention frame portion 104 may tend to lie inside the drug reservoir portion 102 as shown, although the retention frame portion 104 can be positioned inside, outside, above, or below the drug reservoir portion 102 in other cases. At least a portion of the material used to form the device body 106 also is water permeable so that solubilizing fluid (e.g., urine or other bodily fluid) can enter the drug reservoir portion 102 to solubilize the drug units 112 once the device is deployed.

For example, silicone, ethylene vinyl acetate (EVA), thermoplastic polyurethanes, or another biocompatible elastomeric material may be used.

In one embodiment, in which the drug delivery device 100 is designed to be inserted in the bladder, the drug delivery device 100 is designed to be inserted into (and optionally retrieved from) the bladder through the urethra cystoscopically. Thus, the device may be sized and shaped to fit through a narrow tubular path of a deployment instrument, such as a catheter or cystoscope.

The exact configuration and shape of the drug delivery device may be selected depending upon a variety of factors including the specific site of deployment, route of insertion, drug, dosage regimen, and therapeutic application of the device. The design of the device may minimize the patient's pain and discomfort, while locally delivering a therapeutically effective dose of the drug to a tissue site (e.g., urothelial tissue) in a patient.

The Device Body/Drug Reservoir Portion

The drug delivery device has a body, e.g., a housing, that has a drug reservoir, that includes a water-permeable wall, and that includes an elastic portion for engagement with the one or more restraining plugs. The drug reservoir is at least partially defined by the water permeable wall. That is, the device includes a "water-permeable body," which, as the phrase is sometimes used herein, includes any structure having at least a portion that is water-permeable. In embodiments, the water-permeable body is made entirely from a water-permeable material. In other embodiments, the water-permeable body is made from a water-permeable material and a non-water-permeable material. In further embodiments, the water-permeable body is made from a material having at least one water permeable portion and at least one non-water-permeable portion. As used herein, a wall or material is "water-permeable" when it permits a fluid to enter the drug delivery device and contact the drug formulation located in a reservoir within the device body.

The body of the drug delivery devices described herein also includes at least one elastic portion. The elastic portion of the device body may be the same as or distinct from the water permeable portion of the device body described in the preceding paragraph. The restraining plugs contact the at least one elastic portion of the device body to close off an opening the body, which the opening is in fluid communication with the drug reservoir within the device, thereby enclosing the drug within the drug reservoir.

In some embodiments, all of the elastic portions of the device body are contacted with restraining plugs that permit drug release as described herein. In other embodiments, one or more of the elastic portions of the device body are contacted with restraining plugs that permit drug release as described herein and the remaining elastic portions of the body are sealed by other suitable means, such as a cap, an adhesive, heat-sealing, soldering, solvent welding, or a combination thereof.

Generally, the length of the elastic portion should equal or exceed the length of the portion of the restraining plug that contacts the elastic portion of the device body, so that formation/use of the microchannels is not precluded, for example by an inelastic portion of the device body.

In embodiments, the elastic portion of the body is formed from a material that permits the formation of microchannels, or micropathways, between the inner surface of the elastic portion and the restraining plug when hydrostatic pressure builds up in the drug reservoir. The elastic portion may include materials that are water-permeable, water-impermeable, or a combination thereof.

In some embodiments, an agent that increases the osmotic pressure may be disposed in the water-permeable body or included in the drug formulation or, in some embodiments, the drug itself may be an osmotic agent. For example, the drug and osmotic agent can be homogeneously mixed or compressed into tablets. As another example, a drug tablet may be disposed near a restraining plug, and an osmotic agent can be arranged next to the drug tablet. Non-limiting examples of osmotic agents include urea, citric acid, L-tartaric acid, lactose-fructose, dextrose-fructose, sucrose-fructose, mannitol-fructose, sodium chloride, fructose, lactose-sucrose, potassium chloride, lactose-dextrose, mannitol-dextrose, dextrose-sucrose, mannitol-sucrose, sucrose, mannitol-lactose, dextrose, potassium sulfate, mannitol, sodium phosphate tribase.$12H_2O$, sodium phosphate dibasic.$7H_2O$, sodium phosphate dibasic anhydrous, and sodium phosphate monobasic.$H_2O$.

To facilitate the formation of microchannels, the elastic portion of the device body and the restraining plugs may be formed from materials having a certain elasticity or hardness. In embodiments, the Shore durometer of the elastic portion of the body is lower than the Shore durometer of the restraining plug. In one embodiment, the Shore durometer of the elastic portion of the body is from about 40 A to about 60 A, and the Shore durometer of the restraining plug is from about 70 A to about 100 A. In another embodiment, the Shore durometer of the elastic portion of the body is from about 45 A to about 55 A, and the Shore durometer of the restraining plug is from about 75 A to about 85 A. In a further embodiment, the Shore durometer of the elastic portion of the body is about 50 A, and the Shore durometer of the restraining plug is about 80 A. In yet another embodiment, the Shore durometer of the elastic portion of the body is from about 40 A to about 60 A, and the Shore durometer of the restraining plug is about 97 A.

In embodiments, the device body may contain two or more elastic portions having different elasticities that contact two or more restraining plug having different elasticities. This configuration can be useful for controlling drug release from two or more different reservoirs having drugs of different solubilities, desired release rates, etc. For example, a water-permeable body may have a first and a second elastic portion made from two different materials having Shore durometers of 45 A and 55 A, respectively. And inserted into the first and the second elastic portion may be a first and a second restraining plug made from two different materials having Shore durometers of 75 A and 85 A, respectively.

In one embodiment, the device body is made entirely from an elastic material. In other embodiments, the body is made from at least one elastic material and at least one inelastic material. In further embodiments, the body is made from a material having at least one elastic portion and at least one inelastic portion.

The elastic portion of the device body may be any shape that permits the insertion of a restraining plug and the creation of interference fit between the elastic portion and the plug. When viewed in cross-section, the lumen of the elastic portion may be non-polygonal. For example, the cross-section may be round, substantially round, or oval-shaped. In some embodiments, the shape of the lumen of the elastic portion substantially conforms to the shape of the restraining plug.

The device body generally may be made from any biocompatible material, so long as at least a portion of the body is water permeable. The elastic portion of the body that contacts the restraining plug may be made from any biocompatible material that permits the formation of one or more microchannels through which drug may exit the device.

In one embodiment, the device body includes an elongated tube. An interior of the tube may define one or more drug reservoirs, and a drug formulation may be housed in the drug reservoir(s). In other embodiments, the drug reservoir portion is in a form other than a tube. The release rate of the drug from the drug reservoir portion generally is controlled by the design of the combination of the device components, including but not limited to the materials, dimensions, surface area, and restraining plugs, as well as the particular drug formulation and total mass of drug load, among others.

Figure 3:
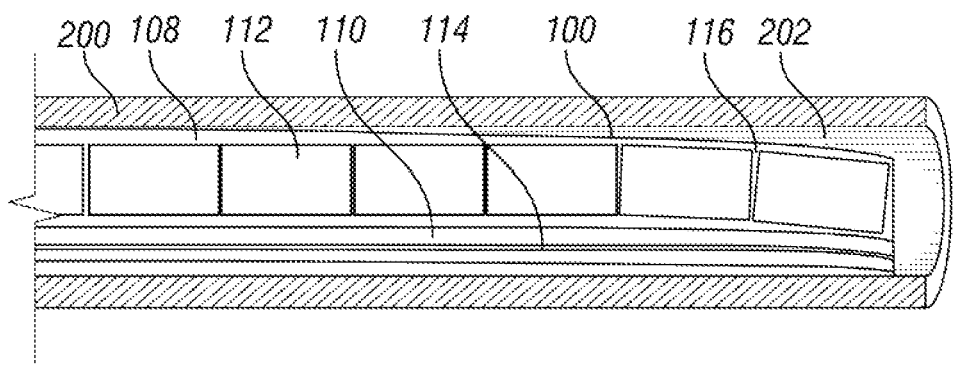
FIG. 3 is a depiction of an embodiment of part of a drug delivery device in a relatively straightened shape inside an insertion instrument.

An example of the drug reservoir portion, i.e., a device body, is shown in FIGS. 2-4. As shown, the drug reservoir portion 102 may include a body formed from an elastomeric tube 122. The tube 122 defines a reservoir 108 that contains a number of drug units 112. Into the openings in the ends of the tube 122, restraining plugs 120 are inserted.

Figure 5A:
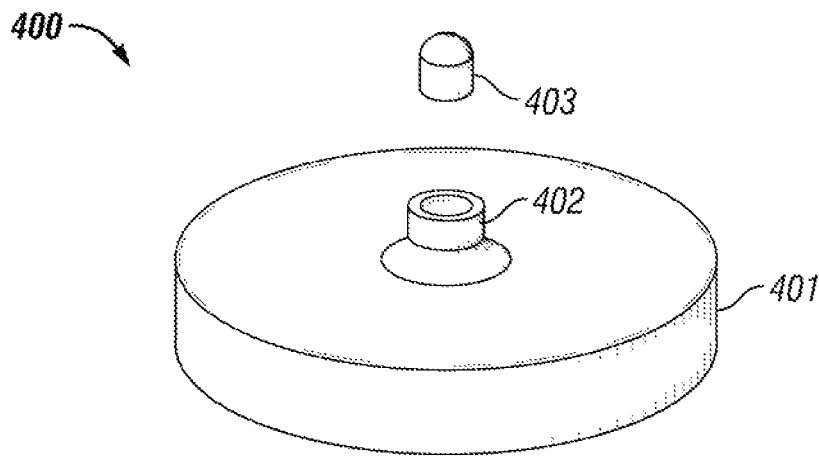
FIGS. 5A-5C show another embodiment of a drug delivery device, with FIG. 5A being a partially exploded perspective view, FIG. 5B being a perspective view of the assembled device, and FIG. 5C being a cross-sectional view of the assembled device.
Figure 5B:
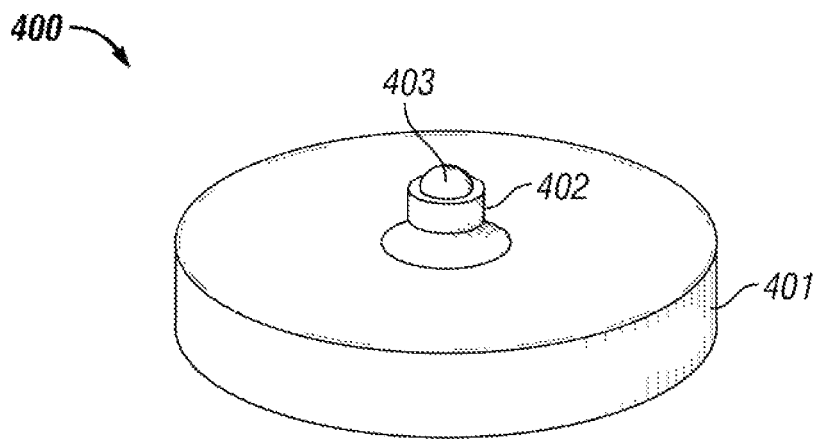
Figure 5C:
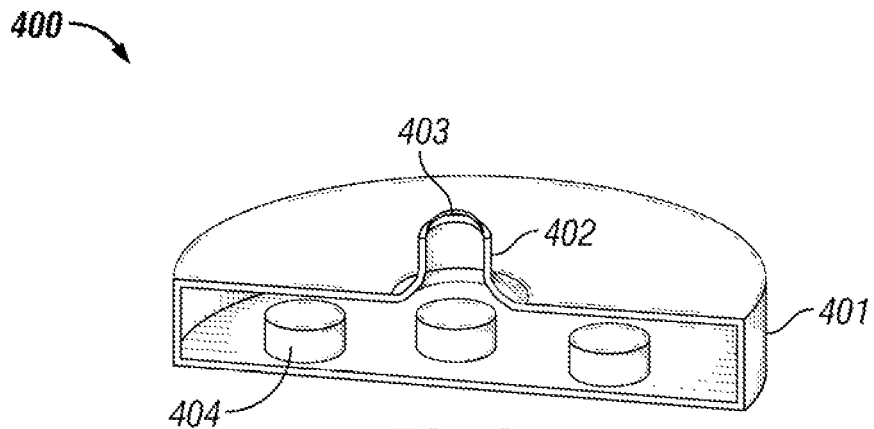

In one embodiment, the drug reservoir portion generally is disk-shaped. One embodiment of a disk-shaped drug reservoir portion is shown in FIGS. 5A-5C. The drug delivery device 400 has a disk-shaped drug reservoir portion 401 having a neck 402. In some embodiments, the neck 402 may not protrude, and is instead embedded in the disk-shaped drug reservoir portion 401 so that the overall device is disk-shaped. The neck 402 is made of an elastic material and the disk-shaped drug reservoir portion 401 is made from a water-permeable material that can be elastic or inelastic. A restraining plug 403 is inserted into the opening of neck 402 to enclose a drug formulation 404 in the disk-shaped drug reservoir portion 401, as shown in FIGS. 5B and 5C. Here, the drug formulation 404 is in the form of a plurality of drug tablets sized to fit through the neck 402. In other variations of this embodiment, the drug formulation may be provided as a single tablet (which may consume all or a significant portion of the drug reservoir volume), or it may be provided in a powder or other solid form or in a liquid, semi-solid, or gel form.

In embodiments, the drug reservoir portion operates as an osmotic pump. In such embodiments, the drug reservoir portion is formed, at least in part, from a water permeable material. In a preferred embodiment, the water permeable material is silicone. Following insertion/implantation into a patient's body, water or urine permeates through a wall of the drug reservoir portion. The water enters the reservoir, contacts the drug formulation, forming a fluidized drug (e.g., a drug solution) which can then be dispensed at a controlled rate out of the reservoir through microchannels that form between the restraining plugs and the elastic portion of the drug reservoir portion. The delivery rate and overall performance of the osmotic pump is affected by device parameters, such as the surface area of the drug reservoir portion; the permeability to liquid of the material used to form the drug reservoir portion; the relative dimensions, shapes, and elasticity or hardness of the restraining plugs and the elastic portion of the drug reservoir lumen; and the drug formulation dissolution profile, among other factors. In some embodiments, the device may initially exhibit a zero-order release rate and subsequently may exhibit a reduced, non-zero-order release rate, in which case the overall drug release profile may be determined by the initial zero-order release rate and the total payload. Representative examples of osmotic pump designs, and equations for selecting such designs, are described in U.S. Patent Publication No. 2009/0149833.

The drug reservoir portion may be formed, at least in part, from an elastomeric material, which may permit elastically deforming the device for its insertion into a patient, e.g., during its deployment through deployment instrument such as a cystoscope or catheter. For example, the tube may be elastically deformed along with the retention frame for intravesical insertion, as described in further detail below.

In one embodiment, the drug reservoir portion is formed from a material that is both elastomeric and water permeable. One material that is both elastomeric and water permeable is silicone, although other biocompatible materials, including inelastic biocompatible materials, may be used.

The length, diameter, and thickness of the drug reservoir portion may be selected based on the volume of drug formulation to be contained, the desired rate of delivery of the drug, the intended site of deployment of the device within the body, the desired mechanical integrity for the device, the desired release rate or permeability to water and urine, the desired induction time before onset of initial release, and the desired method or route of insertion into the body, among others. The tube wall thickness may be determined based on the mechanical properties and water permeability of the tube material, as a tube wall that is too thin may not have sufficient mechanical integrity while a tube wall that is too thick may experience an undesirably long induction time for initial drug release from the device.

In one embodiment, the device body is non-resorbable. It may be formed of medical grade silicone tubing, as known in the art. Other suitable non-resorbable materials may be used. In other embodiments, the device body is at least partially bioerodible. In one embodiment of a bioerodible device, the drug reservoir portion is formed of a biodegradable or bioresorbable polymer. Any suitable polymers may be used.

In embodiments in which the drug reservoir portion is tube-shaped, the drug reservoir portion tube may be substantially linear and in some cases may be substantially cylindrical with a circular or oval cross-section, although square, triangle, hexagon, and other polygonal cross-sectional shapes can be used, among others.

In one embodiment, the drug reservoir portion has multiple reservoirs. Each reservoir may be defined by a portion of the drug reservoir inner surface and at least one partition. In embodiments in which the drug reservoir portion is tube-shaped, the partition may be a partition structure or plug inserted into the tube, such as a cylinder, sphere, or disk, among others, in which case the partition structure may have a larger cross-section than the tube, securing the partition structure in place and segregating adjacent reservoirs. The partition may be non-porous or semi-porous, non-resorbable or resorbable and may be formed of a material described herein with reference to the restraining plugs. The partition also may be formed in the tube, such as by molding. For example, one or more webs may extend through the tube along its length to segregate axial reservoirs that extend along the length of the tube. The partition also may be a structure that joins two different tubes that serve as separate reservoirs.

The multiple reservoirs permit segregating two or more different drug formulations in different reservoirs, delivering a single drug from different reservoirs at different rates or times following deployment, or combinations thereof. For example, two different reservoirs may be in communication with two different restraining plugs having different configurations, as described herein, which permit the drugs in the two different reservoirs to be released at different rates. The two different reservoirs also may house the same or different drug formulations in the same or different forms (such as liquid, semi-solid, and solid), or combinations thereof. Coatings or sheaths also may be provided along different portions of a single drug reservoir or along different drug reservoirs housing the same or different drug formulations. The coatings or sheaths may be used to alter the water-permeability of the water-permeable body. These embodiments can be combined and varied to achieve the desired release profile of the desired drug.

For example, the onset of release of two doses in different reservoirs can be staged by configuring the device accordingly, such as by using different materials (e.g., materials with different water-permeabilities) for portions of the tube defining different reservoirs, by placing drugs with different solubilities in the reservoirs, or by placing drugs with different forms in the reservoirs, such as a liquid form for immediate release and a solid form to be solubilized prior to release. Thus, the device may release some drug relatively quickly after deployment while other drug may experience an induction time before beginning release.

The term "drug" as used herein encompasses any suitable pharmaceutically active ingredient. The drug may be small molecule, macromolecule, biologic, or metabolite, among other forms/types of active ingredients. The drug described herein includes its alternative forms, such as salt forms, free acid forms, free base forms, and hydrates. The drug may be formulated with one or more pharmaceutically acceptable excipients known in the art. Non-limiting examples of the drug include gemcitabine, oxaliplatin, and/or another chemotherapeutic agent; trospium and/or another antimuscarinic agent; and/or lidocaine and/or another anesthetic agent. In one embodiment, the first compartment may be loaded with two or more types of drug tablets (e.g., different drugs), so that a combination of drugs may be delivered.

In embodiments, the drug is one used to treat pain. A variety of anesthetic agents, analgesic agents, and combinations thereof may be used. In one embodiment, the drug is an anesthetic agent. The anesthetic agent may be a cocaine analogue. The anesthetic agent may be an aminoamide, an aminoester, or combinations thereof. Representative examples of aminoamides or amide-class anesthetics include articaine, bupivacaine, carticaine, cinchocaine, etidocaine, levobupivacaine, lidocaine, mepivacaine, prilocalne, ropivacaine, and trimecaine. Representative examples of aminoesters or ester-class anesthetics include amylocalne, benzocaine, butacaine, chloroprocaine, cocaine, cyclomethycaine, dimethocaine, hexylcaine, larocaine, meprylcaine, metabutoxycaine, orthocaine, piperocaine, procaine, proparacaine, propoxycaine, proxymetacaine, risocaine, and tetracaine. The drug also can be an antimuscarinic compound that exhibits an anesthetic effect, such as oxybutynin or propiverine. In embodiments, the analgesic agent includes an opioid. Representative examples of opioid agonists include alfentanil, allylprodine, alphaprodine, anileridine, benzyl morphine, bezitramide, buprenorphine, butorphanol, clonitazene, codeine, desomorphine, dextromoramide, dezocine, diampromide, diamorphone, dihydrocodeine, dihydromorphine, dimenoxadol, dimepheptanol, di methylthiambutene, dioxaphetyl butyrate, dipipanone, eptazocine, ethoheptazine, ethylmethylthiambutene, ethylmorphine, etonitazene fentanyl, heroin, hydrocodone, hydromorphone, hydroxypethidine, isomethadone, ketobemidone, levorphanol, levophenacylmorphan, lofentanil, meperidine, meptazinol, metazocine, methadone, metopon, morphine, myrophine, nalbuphine, narceine, nicomorphine, norlevorphanol, normethadone, nalorphine, normorphine, norpipanone, opium, oxycodone, oxymorphone, papaveretum, pentazo- cine, phenadoxone, phenomorphan, phenazocine, phenoperidine, piminodine, piritramide, proheptazine, promedol, properidine, propiram, propoxyphene, sufentanil, tilidine, tramadol, pharmaceutically acceptable salts thereof, and mixtures thereof. Other opioid drugs, such as mu, kappa, delta, and nociception opioid receptor agonists, are contemplated. Representative examples of other suitable pain relieving agents include such agents as salicyl alcohol, phenazopyridine hydrochloride, acetaminophen, acetylsalicylic acid, flufenisal, ibuprofen, indoprofen; indomethacin, naproxen.

In certain embodiments, the drug is one used to treat inflammatory conditions such as interstitial cystitis, radiation cystitis, painful bladder syndrome, prostatitis, urethritis, post-surgical pain, and kidney stones. Non-limiting examples of drugs for these conditions include lidocaine, glycosaminoglycans (e.g., chondroitin sulfate, sulodexide), pentosan polysulfate sodium (PPS), dimethyl sulfoxide (DMSO), oxybutynin, mitomycin C, heparin, flavoxate, ketorolac, or a combination thereof. Other non-limiting examples of drugs that may be used in the treatment of IC include nerve growth factor monoclonal antibody (MAB) antagonists, such as Tanezumab, and calcium channel alpha-2-delta modulators, such as PD-299685 or gabepentin.

In certain embodiments, the drug is one used to treat urinary incontinence, frequency, or urgency, including urge incontinence and neurogenic incontinence, as well as trigonitis. Drugs that may be used include anticholinergic agents, antispasmodic agents, anti-muscarinic agents, β-2 agonists, alpha adrenergics, anticonvulsants, norepinephrine uptake inhibitors, serotonin uptake inhibitors, calcium channel blockers, potassium channel openers, and muscle relaxants. Representative examples of suitable drugs for the treatment of incontinence include oxybutynin, S-oxybutylin, emepronium, verapamil, imipramine, flavoxate, atropine, propantheline, tolterodine, rociverine, clenbuterol, darifenacin, terodiline, trospium, hyoscyamin, propiverine, desmopressin, vamicamide, clidinium bromide, dicyclomine HCl, glycopyrrolate aminoalcohol ester, ipratropium bromide, mepenzolate bromide, methscopolamine bromide, scopolamine hydrobromide, iotropium bromide, fesoterodine fumarate, YM-46303 (Yamanouchi Co., Japan), lanperisone (Nippon Kayaku Co., Japan), inaperisone, NS-21 (Nippon Shinyaku Orion, Formenti, Japan/Italy), NC-1800 (Nippon Chemiphar Co., Japan), Z D-6169 (Zeneca Co., United Kingdom), and stilonium iodide.

In certain embodiments, the drug is one used to treat urinary tract cancer, such as bladder cancer and prostate cancer. Drugs that may be used include antiproliferative agents, cytotoxic agents, chemotherapeutic agents, or a combination thereof. Representative examples of drugs which may be suitable for the treatment of urinary tract cancer include *Bacillus* Calmette Guerin (BCG) vaccine, cisplatin, doxorubicin, valrubicin, gemcitabine, mycobacterial cell wall-DNA complex (MCC), methotrexate, vinblastine, thiotepa, mitomycin, fluorouracil, leuprolide, diethylstilbestrol, estramustine, megestrol acetate, cyproterone, flutamide, a selective estrogen receptor modulators (i.e. a SERM, such as tamoxifen), botulinum toxins, and cyclophosphamide. The drug may be a biologic, and it may comprise a monoclonal antibody, a TNF inhibitor, an anti-leukin, or the like. The drug also may be an immunomodulator, such as a TLR agonist, including imiquimod or another TLR7 agonist. The drug also may be a kinase inhibitor, such as a fibroblast growth factor receptor-3 (FGFR3)-selective tyrosine kinase inhibitor, a phosphatidylinositol 3 kinase (PI3K) inhibitor, or a mitogen-activated protein kinase (MAPK) inhibitor, among others or combinations thereof. Other examples include celecoxib, erolotinib, gefitinib, paclitaxel, polyphenon E, valrubicin, neocarzinostatin, apaziquone, Belinostat, Ingenol mebutate, Urocidin (MCC), Proxinium (VB 4845), BC 819 (BioCancell Therapeutics), Keyhole limpet haemocyanin, LOR 2040 (Lorus Therapeutics), urocanic acid, OGX 427 (OncoGenex), and SCH 721015 (Schering-Plough). Other intravesical cancer treatments include small molecules, such as Apaziquone, adriamycin, AD-32, doxorubicin, doxetaxel, epirubicin, gemcitabine, HTI-286 (hemiasterlin analogue), idarubicin, γ-linolenic acid, mitozantrone, meglumine, and thiotepa; large molecules, such as Activated macrophages, activated T cells, EGF-dextran, HPC-doxorubicin, IL-12, IFN-α2b, IFN-γ, α-lactalbumin, p53 adenovector, TNFα; combinations, such as Epirubicin+BCG, IFN+farmarubicin, Doxorubicin+5-FU (oral), BCG+IFN, and Pertussis toxin+cystectomy; activated cells, such as macrophages and T cells; intravesical infusions such as IL-2 and Doxorubicin; chemosensitizers, such as BCG+antifirinolytics (paramethylbenzoic acid or aminocaproic acid) and Doxorubicin+verapimil; diagnostic/imaging agents, such as Hexylaminolevulinate, 5-aminolevulinic acid, Iododexyuridine, HMFG1 Mab+Tc99m; and agents for the management of local toxicity, such as Formaline (hemorrhagic cystitis).

In certain embodiments, the drug is one used to treat infections involving the bladder, the prostate, and the urethra. Antibiotics, antibacterial, antifungal, antiprotozoal, antiseptic, antiviral and other antiinfective agents can be administered for treatment of such infections. Representative examples of drugs for the treatment of infections include mitomycin, ciprofloxacin, norfloxacin, ofloxacin, methanamine, nitrofurantoin, ampicillin, amoxicillin, nafcillin, trimethoprim, sulfonamides trimethoprimsulfamethoxazole, erythromycin, doxycycline, metronidazole, tetracycline, kanamycin, penicillins, cephalosporins, and aminoglycosides.

In certain embodiments, the drug is one used to treat fibrosis of a genitourinary site, such as the bladder or uterus. Representative examples of drugs for the treatment of fibroids include pentoxphylline (xanthine analogue), antiTNF, antiTGF agents, GnRH analogues, exogenous progestins, antiprogestins, selective estrogen receptor modulators, danazol and NSAIDs.

In certain embodiments, the drug is one used to treat neurogenic bladder. Representative examples of such drugs include analgesics or anaesthetics, such as lidocaine, bupivacaine, mepivacaine, prilocalne, articaine, and ropivacaine; anticholinergics; antimuscarinics such as oxybutynin or propiverine; a vanilloid, such as capsaicin or resiniferatoxin; antimuscarinics such as ones that act on the M3 muscarinic acetylcholine receptor (mAChRs); antispasmodics including $GABA_B$ agonists such as baclofen; botulinum toxins; capsaicins; α-adrenergic antagonists; anticonvulsants; serotonin reuptake inhibitors such as amitriptyline; and nerve growth factor antagonists. In various embodiments, the drug may be one that acts on bladder afferents or one that acts on the efferent cholinergic transmission, as described in Reitz et al., Spinal Cord 42:267-72 (2004).

In certain embodiments, the drug is one used to treat incontinence due to neurologic detrusor overactivity and/or low compliant detrusor. Examples of these types of drugs include bladder relaxant drugs (e.g., oxybutynin (antimuscarinic agent with a pronounced muscle relaxant activity and local anesthetic activity), propiverine, impratroprium, tiotropium, trospium, terodiline, tolterodine, propantheline, oxyphencyclimine, flavoxate, and tricyclic antidepressants; drugs for blocking nerves innervating the bladder and urethra (e.g., vanilloids (capsaicin, resiniferatoxin), botulinum-A toxin); or drugs that modulate detrusor contraction strength, micturition reflex, detrusor sphincter dyssynergia (e.g., GABAb agonists (baclofen), benzodiazapines). In another embodiment, the drug is selected from those known for the treatment of incontinence due to neurologic sphincter deficiency. Examples of these drugs include α-adrenergic agonists, estrogens, β-adrenergic agonists, tricyclic antidepressants (imipramine, amitriptyline). In still another embodiment, the drug is selected from those known for facilitating bladder emptying (e.g., α-adrenergic antagonists (phentolamitie) or cholinergics). In yet another embodiment, the drug is selected from among anticholinergic drugs (e.g., dicyclomine), calcium channel blockers (e.g., verapamil) tropane alkaloids (e.g., atropine, scopolamine), nociceptin/orphanin FQ, and bethanechol (e.g., M3 muscarinic agonist, choline ester).

Restraining Plugs

The restraining plugs may have any shape suitable for placement in the one or more elastic portions of the body that permits the formation of microchannels as described herein. In embodiments, the restraining plugs are cylindrical or substantially cylindrical. As used herein, the term "substantially cylindrical" refers to any shape that is non-polygonal when viewed in cross-section. In other embodiments, the restraining plugs are partially cylindrical or substantially cylindrical, and have at least one portion that is wedged, tapered, angled, or rounded.

FIG. 6 depicts a series of restraining plugs 502, 503, 504, 505, and 506 having different shapes. FIG. 7 depicts the restraining plugs 502, 503, 504, 505, and 506 inserted into a tube-shaped elastic portion 501 of a device body. When the restraining plug has a wedged, tapered, angled, or rounded surface, these surfaces may allow the microchannels described herein to form more easily. Not wishing to be bound by any particular theory, it is believed that the wedged, tapered, angled, or rounded surfaces may provide a preferential path for osmotic flow along or near such surfaces. As a result, less hydrostatic pressure may be required to create one or more microchannels between the restraining plug and the elastic portion of the water-permeable body. Generally, the restraining plugs may have one or more wedged, tapered, angled, or rounded surfaces on one side or both sides of the restraining plugs' longitudinal axis. In embodiments, the angle between the longitudinal surface of the restraining plug and the surface of the wedged, tapered, angled, or rounded portion may be from about 30° to about 60°.

As shown in FIG. 7, the wedged, tapered, angled, or rounded surfaces of the restraining plugs 502, 503, 504, 505, 506 can be inserted into the end of the tube-shaped elastic portion 501 so that the wedged, tapered, angled, or rounded surfaces of the restraining plugs are in communication with the interior (drug reservoir) of the drug delivery devices. In FIG. 7, the opposed base of the restraining plugs faces outward, as an exterior surface of the drug delivery devices. Alternatively, in other embodiments, the position may be reversed, so that the wedged, tapered, angled, or rounded surfaces of the restraining plug face outward, as an exterior surface of the drug delivery devices, while the base of the restraining plug is in communication with the interior (drug reservoir) of the drug delivery devices. In this position, the wedged, tapered, angled, or rounded surfaces of the restraining plugs may create a void space at or near the end of the elastic portion. The void space or a portion thereof may host an adhesive, clamp, plug, or other known means for securing the restraining plug, as illustrated in FIG. 20B.

The restraining plugs should contact the elastic portions of the water-permeable body in a manner that prohibits the restraining plug from being expelled from the elastic portion when the device is compressed in the body after deployment and/or when a hydrostatic force is exerted on the restraining plug. In embodiments, there is interference, friction, or press fit present between the restraining plug and the elastic portion. Where applicable, the restraining plug also should remain in the elastic portion of the water-permeable body when the device is elastically deformed between its retention shape and relatively straightened shape.

In a preferred embodiment, the restraining plugs do not migrate within the elastic portions of the device body after deployment and during drug release. In other embodiments, the restraining plugs do migrate within the elastic portions of the water-permeable body after deployment and during drug release. Migration of the restraining plugs can be tolerated as long as the drug release is not undesirably affected.

In embodiments, the cross-sectional shape of the restraining plugs substantially conforms to the inner dimensions of the elastic portion of the device body. In other embodiments, the outer diameter of the restraining plugs exceeds the inner diameter of the elastic portion of the device body. The phrase "inner diameter," as used herein, is not intended to imply that the elastic portion is always circular when viewed in cross-section; instead, the term refers to the largest diameter or major axis of the lumen of the elastic portion of the water-permeable body. Similarly, the phrase "outer diameter," as used herein, is not intended to imply that the restraining plug, when viewed in cross-section, is always circular; instead, the term refers to the largest diameter or major axis of the cross-section of the restraining plug or its base.

In one embodiment, the outer diameter of the restraining plug exceeds the inner diameter of the elastic portion of the device body by at least 3%. In another embodiment, the outer diameter of the restraining plug exceeds the inner diameter of the elastic portion of the device body by at least 5%. In yet another embodiment, the outer diameter of the restraining plug exceeds the inner diameter of the elastic portion of the device body by at least 10%. In a further embodiment, the outer diameter of the restraining plug exceeds the inner diameter of the elastic portion of the device body by at least 15%. In a still further embodiment, the outer diameter of the restraining plug exceeds the inner diameter of the elastic portion of the device body by at least 20%. In a particular embodiment, the outer diameter of the restraining plug exceeds the inner diameter of the elastic portion of the body by at least 25%.

In one embodiment, the outer diameter of the restraining plug exceeds the inner diameter of the elastic portion of the device body by about 5%, and the inner diameter of the elastic portion of the device body is 2.16 mm and the outer diameter of the restraining plug is 2.27 mm. The restraining plug, in this embodiment, has a length of from about 2.5 mm to about 5 mm.

In another embodiment, the outer diameter of the restraining plug exceeds the inner diameter of the elastic portion of the water-permeable body by about 28%. For example, in one case, the inner diameter of the elastic portion of the water-permeable body is 2.16 mm and the other diameter of the restraining plug is 2.77 mm. The restraining plug, in this embodiment, has a length of from about 2.5 mm or 5 mm long.

The restraining plugs may be of any length that is suited for allowing the formation of microchannels between the restraining plug and the elastic portion of the device body. The outer surface of the restraining plug may contact the inner surface of the elastic portion of the device body along the entire length of the restraining plug or for only a portion of the restraining plug's length. For example, the outer surface of a restraining plug shaped like a cylinder may contact the inner surface of the opening in the elastic portion of the water-permeable body along the entire length of the restraining plug. The outer surface of a restraining plug having one or more wedged, angled, or tapered surfaces, however, may only contact the inner surface of the elastic portion of the water-permeable body along a portion of the restraining plug's overall length, as shown, for example, in FIGS. 7 and 20B.

In embodiments, the length of the restraining plug may be from about 2 mm to about 10 mm, from about 2 mm to about 8 mm, from about 2 to about 6 mm, or from about 2.5 mm to about 5 mm.

Generally, the inner surface of the elastic portion of the water-permeable body and the restraining plug may be shaped so that the restraining plug and the elastic portion of the water-permeable body remain in contact with each other during deployment. In some embodiments, adhesive may be used to secure together the elastic portion of the water-permeable body and the restraining plug. A single portion or one or more discrete portions of adhesive may be used as long as the amount and placement of adhesive does not undesirably impact the drug release as described herein. In other embodiments, the restraining plug may be secured mechanically. For example, an external clamp may be used to secure together the elastic portion of the water-permeable body and the restraining plug. Any suitable clamp may be used as long as it does not undesirably impact tolerability of the device to the patient or the drug release as described herein. When the restraining plug is secured mechanically, with adhesive, or both, it may be necessary to form the elastic portion or the restraining plug or both with a softer material to ensure the formation of microchannels.

The restraining plugs may be made from any biocompatible material or combination of biocompatible materials that permits the release of drug from the device as described herein. For example, the restraining plugs may be made from a polymer, such as silicone or ethylene vinyl acetate, a ceramic, an adhesive, or a combination thereof. The material may be biodegradable or bioerodible.

The Retention Frame Portion

In a preferred embodiment, the drug delivery device includes a retention frame portion. The retention frame portion is associated with the drug reservoir portion and permits retaining the drug reservoir portion in the body, such as in the bladder. The retention frame portion may include a retention frame that is deformable between a relatively expanded shape and a relatively lower-profile shape. For example, the retention frame may naturally assume the relatively expanded shape, may be manipulated into the relatively lower-profile shape for insertion into the body, and may spontaneously return to the relatively expanded shape upon insertion into the body. The retention frame in the relatively expanded shape may be shaped for retention in a body cavity, and the retention frame in the relatively lower-profile shape may be shaped for insertion into the body through the working channel of a deployment instrument such as a catheter or cystoscope. To achieve such a result, the retention frame may have an elastic limit, modulus, and/or spring constant selected to impede the device from assuming the relatively lower-profile shape once deployed. Such a configuration may limit or prevent accidental expulsion of the device from the body under expected forces. For example, the device may be retained in the bladder during urination or contraction of the detrusor muscle.

In a preferred embodiment, the retention frame includes or consists of an elastic wire. The elastic wire also may include a relatively low modulus elastomer, which may be relatively less likely to irritate or cause ulcer within the bladder or other deployment site and may be biodegradable so that the device need not be removed.

For example, in the embodiment shown in FIGS. 2-3, the retention frame 114 is an elastic wire formed from a superelastic alloy, such as nitinol, and surrounded by the wall 124 of the retention frame lumen 110, which forms a protective sheath about the retention frame 114. The wall 124 may be formed from a polymer material, such as silicone. In other embodiments, the retention frame may be an elastic wire formed from a superelastic alloy, such as nitinol, that is covered in a polymer coating such as a silicone sheath and is attached to the drug reservoir portion.

In some embodiments, the retention frame lumen 110 may include the retention frame 114 and a filling material, such as a polymer filling. An example filling material is a silicone adhesive, such as MED3-4213 by Nusil Technology LLC, although other filling materials may be used. The filling material may completely or partially fill the void in the retention frame lumen 110 about the retention frame 114. For example, the filling material may be poured into the retention frame lumen 110 about the retention frame 114 and may cure therein. The filling material may reduce the tendency of the drug reservoir lumen 108 to stretch along, or twist or rotate about, the retention frame 114, while maintaining the drug reservoir lumen 108 in a selected orientation with reference to the retention frame 114. The filling material is not necessary, however, and may be omitted.

When the retention frame is in the relatively expanded shape, such as the coiled shape shown in FIG. 2, the device may occupy a space having dimensions suited to impede expulsion from the bladder. When the retention frame is in the relatively lower-profile shape, such as the elongated shape shown in FIG. 3, the device may occupy an area suited for insertion into the body, such as through the working channel of a deployment instrument. The properties of the elastic wire cause the device to function as a spring, deforming in response to a compressive load but spontaneously returning to its initial shape once the load is removed.

A retention frame that assumes a pretzel shape may be relatively resistant to compressive forces. The pretzel shape essentially comprises two sub-circles, each having its own smaller arch and sharing a common larger arch. When the pretzel shape is first compressed, the larger arch absorbs the majority of the compressive force and begins deforming, but with continued compression the smaller arches overlap, and subsequently, all three of the arches resist the compressive force. The resistance to compression of the device as a whole increases once the two sub-circles overlap, impeding collapse and voiding of the device as the bladder contracts during urination.

In embodiments in which the retention frame comprises a shape-memory material, the material used to form the frame may "memorize" and spontaneously assume the relatively expanded shape upon the application of heat to the device, such as when exposed to body temperatures upon entering the bladder.

The retention frame may be in a form having a high enough spring constant to retain the device within a body cavity, such as the bladder. A high modulus material may be used, or a low modulus material. Especially when a low-modulus material is used, the retention frame may have a diameter and/or shape that provides a spring constant without which the frame would significantly deform under the forces of urination. For example, the retention frame may include one or more windings, coils, spirals, or combinations thereof, specifically designed to achieve a desirable spring constant as described in US Application Publication No. 2009/0149833.

The retention frame may have a two-dimensional structure that is confined to a plane, a three-dimensional structure, such as a structure that occupies the interior of a spheroid, or some combination thereof.

II. Use and Applications of the Device

The device may be deployed in a body cavity or lumen, and subsequently may release one or more drugs for the treatment of one or more conditions, locally to one or more tissues at the deployment site and/or regionally to other tissues distal from the deployment site. The release may be controlled over an extended period. Thereafter, the device may be removed, resorbed, excreted, or some combination thereof.

Figure 8:
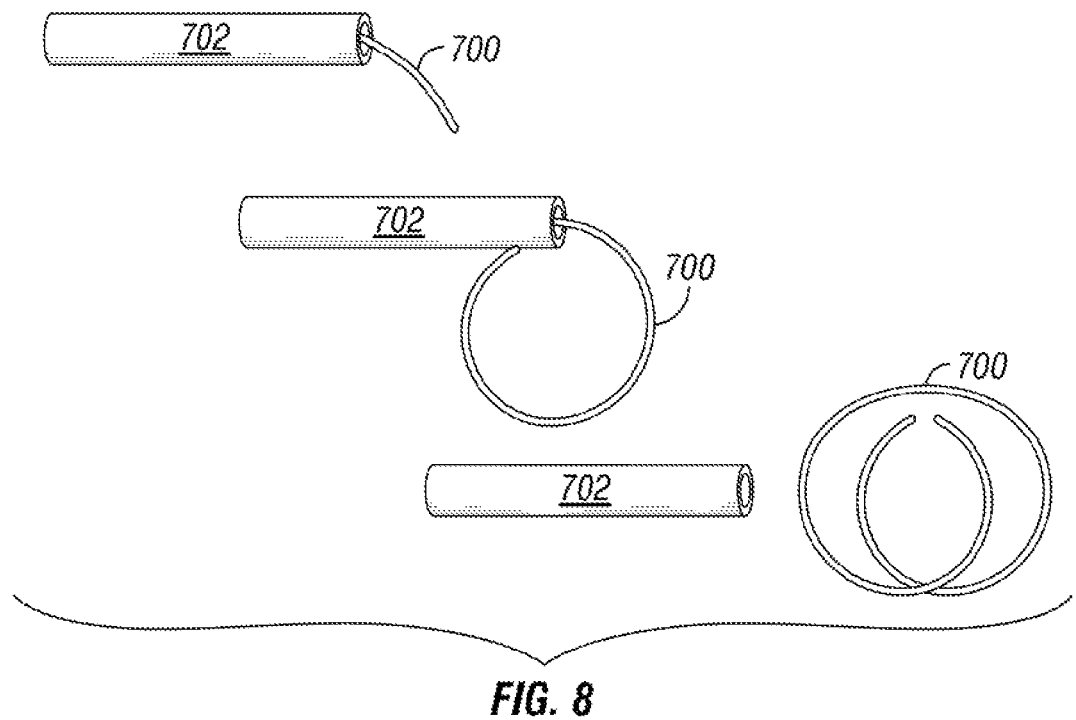
FIG. 8 depicts an embodiment of a drug delivery device assuming a retention shape as the device exits a deployment instrument.

In one example, the device is inserted into the body by passing the drug delivery device through a deployment instrument and releasing the device from the deployment instrument into the body. In cases in which the device is deployed into a body cavity such as the bladder, the device assumes a retention shape, such as an expanded or higher profile shape, once the device emerges from the deployment instrument into the cavity. An example is illustrated in FIG. 8, which shows the device 700 assuming a retention shape as the device exits a deployment instrument 702. The deployment instrument 702 may be any suitable lumen device, such as a catheter, urethral catheter, or cystoscope. The deployment instrument 702 may be a commercially available device or a device specially adapted for the present drug delivery devices, for example, as described in U.S. Patent Application Publication No. 2011/0202036.

Once inserted into the body, the device releases the drug in a controlled manner. The device may provide extended, continuous, intermittent, or periodic release of a desired quantity of drug over a desired, predetermined time period. In embodiments, the device can deliver the desired dose of drug over an extended period, such as 12 hours, 24 hours, 5 days, 7 days, 10 days, 14 days, or 20, 25, 30, 45, 60, or 90 days, or more. The rate of delivery and dosage of the drug can be selected depending upon the drug being delivered and the disease or condition being treated.

In embodiments in which the device comprises a drug in a solid form, elution of drug from the device occurs following dissolution of the drug within the device. Bodily fluid enters the device, contacts the drug and solubilizes the drug, and thereafter the dissolved drug exits the device via the microchannels described herein. For example, the drug may be solubilized upon contact with urine in cases in which the device is deployed in the bladder.

Subsequently, the device may be retrieved from the body, such as in cases in which the device is non-resorbable, non-collapsible, or otherwise needs to be removed.

The device also may be configured to be completely or partially bioresorbable, such that retrieval is unnecessary. In one case, the device is resorbed or sufficiently degraded that it can be expelled from the bladder during urination. In particular embodiments, the device include biodegradable links such that the device can collapse into a shape that permits passage through the urethra during urination, as described in U.S. Patent Application Publication No. 2012/0089122, which is incorporated herein by reference. The device may not be retrieved or resorbed until some of the drug, or preferably most or the entire drug, has been released.

Figure 9:
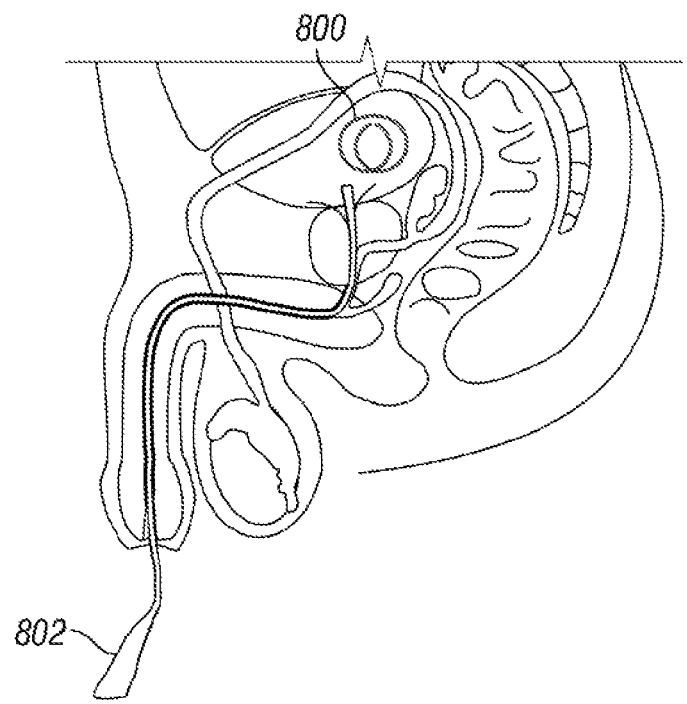
FIG. 9 is a cross-sectional view depicts the deployment of a drug delivery device into the bladder of a patient.

FIG. 9 illustrates the deployment of a device 800 into the bladder, wherein the adult human male anatomy is shown by way of example. A deployment instrument 802 may be inserted through the urethra to the bladder, and the device 800 may be passed through the deployment instrument 802, driven by a stylet and/or a flow of lubricant or other fluid, for example, until the device 800 exits into the bladder. Thus, the device is deployed into the bladder of a male or female human patient in need of treatment.

The device may be deployed into the bladder of a patient in an independent procedure or in conjunction with another urological or other procedure or surgery, either before, during, or after the other procedure. The device may release one or more drugs that are delivered to local and/or regional tissues for therapy or prophylaxis, either peri-operatively, post-operatively, or both.

In one embodiment, the drug delivery device, with a self-contained drug payload, is deployed wholly within the bladder to provide sustained delivery of at least one drug to the bladder in an amount that is therapeutically effective for the target tissue in need of treatment. It may be the bladder itself or regionally proximate to the bladder. Such regional delivery may provide an alternative to systemic administration, which may entail undesirable side effects or result in insufficient bioavailability of the drug. Following in vivo deployment of the device, at least a portion of the payload of drug is released from the device substantially continually over an extended period, to the urothelium and possibly to nearby tissues, in an amount effective to provide treatment or to improve bladder function in the patient. In a preferred embodiment, the device resides in the bladder releasing the drug over a predetermined period, such as two weeks, three weeks, four weeks, a month, or more.

In such cases, the device may be used to treat interstitial cystitis, radiation cystitis, pelvic pain, overactive bladder syndrome, bladder cancer, neurogenic bladder, neuropathic or non-neuropathic bladder-sphincter dysfunction, infection, post-surgical pain or other diseases, disorders, and conditions treated with drugs delivered to the bladder. The device may deliver drugs that improve bladder function, such as bladder capacity, compliance, and/or frequency of uninhibited contractions, that reduce pain and discomfort in the bladder or other nearby areas, or that have other effects, or combinations thereof. The bladder-deployed device also may deliver a therapeutically effective amount of one or more drugs to other genitourinary sites within the body, such as other locations within urological or reproductive systems of the body, including one or both of the kidneys, the urethra, one or both of the ureters, the penis, the testes, one or both of the seminal vesicles, one or both of the vas deferens, one or both of the ejaculatory ducts, the prostate, the vagina, the uterus, one or both of the ovaries, or one or both of the fallopian tubes, among others or combinations thereof. For example, the intravesical drug delivery device may be used in the treatment of kidney stones or fibrosis, erectile dysfunction, among other diseases, disorders, and conditions.

In one embodiment, the intravesical drug delivery device is deployed into a bladder to locally deliver lidocaine or another anesthetic agent for management of pain arising from any source, such as a disease or disorder in genitourinary tissues, or pain stemming from any bladder procedure, such as surgery, catheterization, ablation, medical device implantation, or stone or foreign object removal, among others.

In embodiments, the drug delivery device is sterilized, such as after the device is manufactured/assembled and before the device is deployed into the patient. In some cases, the device may be sterilized after the device is packaged, such as by subjecting the package to gamma irradiation, electron beam irradiation, or ethylene oxide gas. Although gamma irradiation may affect the performance of certain aspects of the drug delivery devices, materials and configurations can be chosen, as explained herein, to eliminate or substantially neutralize any adverse effects.

The present invention may be further understood with reference to the following non-limiting examples.

III. Examples

Example 1—Comparison of Various System Configurations

Three drug delivery devices (FIGS. 10A-10C) with different system configurations were made and their in vitro drug release profiles were measured. Each of the three devices had an elastic body made of silicone with a drug reservoir lumen (901, 910, 920) and a retention frame lumen (903, 912, 922).

The retention frame lumen of each device housed a retention frame (904, 913, 923) made from nitinol wire. The nitinol wire kept the devices in the above-described "pretzel" retention shape when unstressed. The three drug devices in FIGS. 10A-10C are shown in a relatively straightened shape.

The drug reservoir lumen of each device had an internal diameter of 2.64 mm, and the drug reservoir lumens' walls were 0.2 mm thick. The drug housed in each drug delivery device in this example was lidocaine hydrochloride monohydrate (LHM) tablets (89.5% LHM, 2.5% PVP, 8% PEG 8000).

The first configuration, shown in FIG. 10A (Type A device) included a drug reservoir lumen 901 with two ends. The drug reservoir lumen 901 contained LHM tablets (89.5% LHM, 2.5% PVP, 8% PEG 8000) 902. In one end of the drug reservoir lumen 901 was inserted a restraining plug 905 and silicone adhesive 906, which sealed that end of the drug reservoir lumen 901 to prevent the release of drug from that end. The restraining plug 905 was inserted into the drug reservoir lumen 901 far enough to allow the silicone adhesive 906 to be placed in the drug reservoir lumen 901. Into the other end of the drug reservoir lumen 901 was inserted a plug 907 having an orifice 908. The orifice 908 had an internal diameter of 0.3 mm, and the plug 907 had an outer diameter of 2.64 mm and a length of 5.0 mm. The outer surface of the orifice 908 was sealed with silicone adhesive. The drug reservoir lumen housed a payload of 600 mg of lidocaine (free base equivalent, or FBE) tablets.

The second configuration, shown in FIG. 10B (Type B device) included a drug reservoir lumen 910, and into each end of the drug reservoir lumen was inserted a restraining plug 914, 915. The restraining plugs had a length of 5.0 mm and an outer diameter of 2.77 mm. Therefore, in this configuration, the restraining plugs' outer diameter was about 5% larger than the internal diameter of the drug reservoir lumen 910, which was 2.64 mm. The drug reservoir lumen 910 housed 660 mg of lidocaine FBE tablets 911. No silicone adhesive was used in this configuration.

The third configuration, shown in FIG. 10C (Type C device) was identical to the preceding second configuration, except the third configuration contained one end having a restraining plug 925 and sealed with silicone adhesive 926, thereby preventing the release of drug from the sealed end. The restraining plug 925 was inserted far enough into the device to allow the silicone adhesive 926 to be placed in the drug reservoir lumen 920. The drug reservoir lumen 920 housed 660 mg of lidocaine FBE tablets 921.

Figure 11:
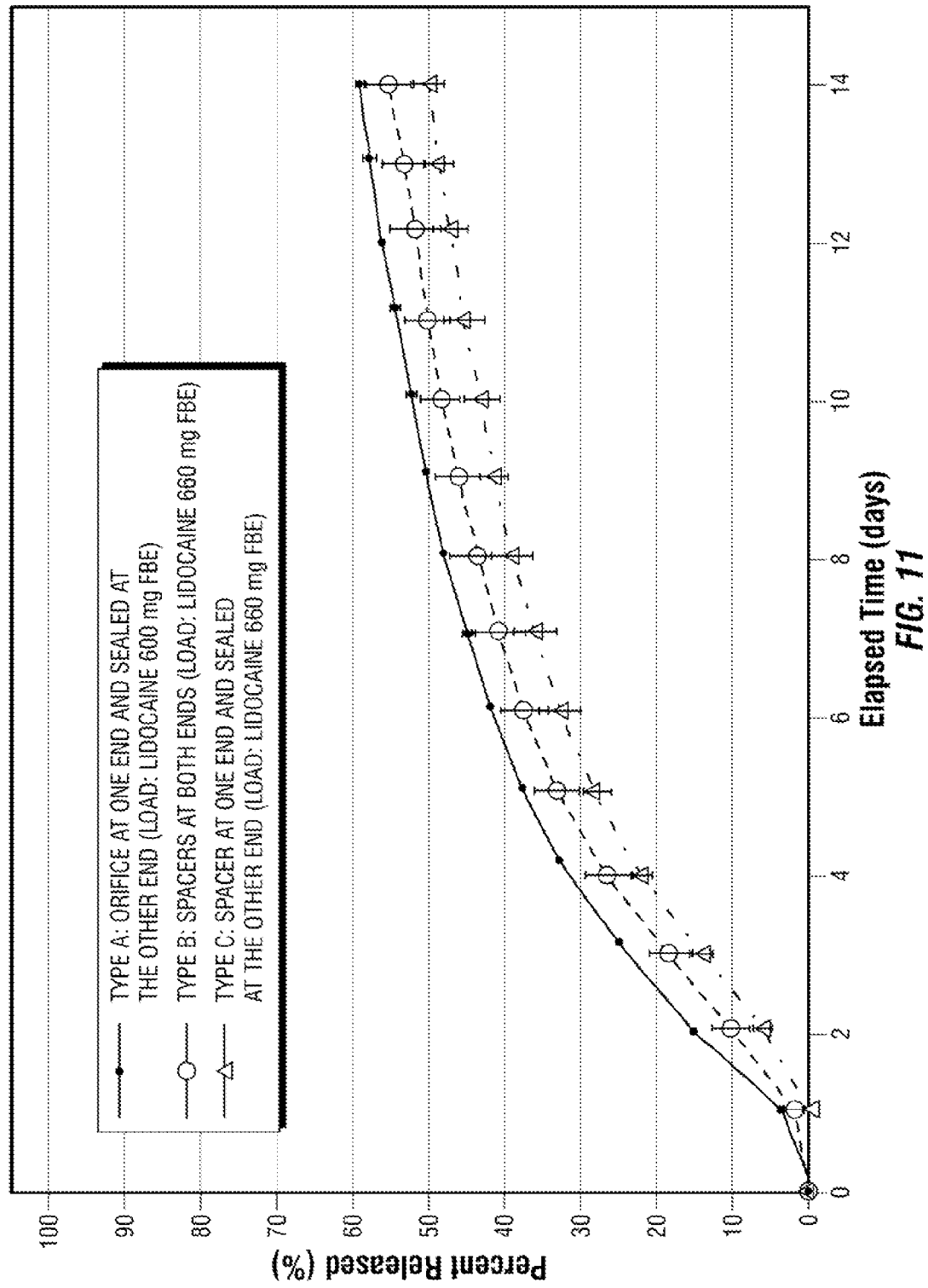
FIG. 11 is a graph showing the percentage of drug released in vitro over time by three devices during a test.

The in vitro release profiles were measured for the three devices types. The devices were placed in deionized water at 37° C., and the drug release percentage was measured over 14 days. To ensure reproducibility, the release profiles of three devices of each configuration were measured, i.e., three Type A devices, three Type B devices, and three Type C devices. The average release profiles for the devices are shown in FIG. 11. The error bars in FIG. 11 represent standard deviation around the mean. The data indicate that the devices of all three configurations had similar in vitro drug release profiles, the drug release occurring through the microchannels described herein.

Example 2—Water Displacement Test

The mass loss from a variety of devices filled with water after a single compression was measured. Before compressing the devices, each was filled with water instead of a drug formulation. To enable water filling and sealing, each device was fitted with access port tubing.

Each dry device was weighed before being filled with deionized water through the access ports using a dispensing tip. The ports were sealed with a smooth face clip once the devices were filled. The filled devices were then weighed while in an unstressed position. The unstressed devices were then placed on a flat surface, and compressed along the devices' long axis up to a pre-determined gap of 2 or 3 cm. In other words, the unstressed devices, which measured about 4 cm along their long axes, were compressed into a gap or space of 2 or 3 cm by a compressive force. The compressive force was applied along the devices' long axes. The devices were compressed for 15 seconds. For the devices containing at least one orifice, the water that appeared at the orifice was removed with a delicate task wiper.

The compressive force was then removed, and the devices were allowed to return to their unstressed position. Any remaining water on the surfaces of the devices was removed with a delicate task wiper. The devices were then weighed and the water loss of each device was calculated.

Figure 12:
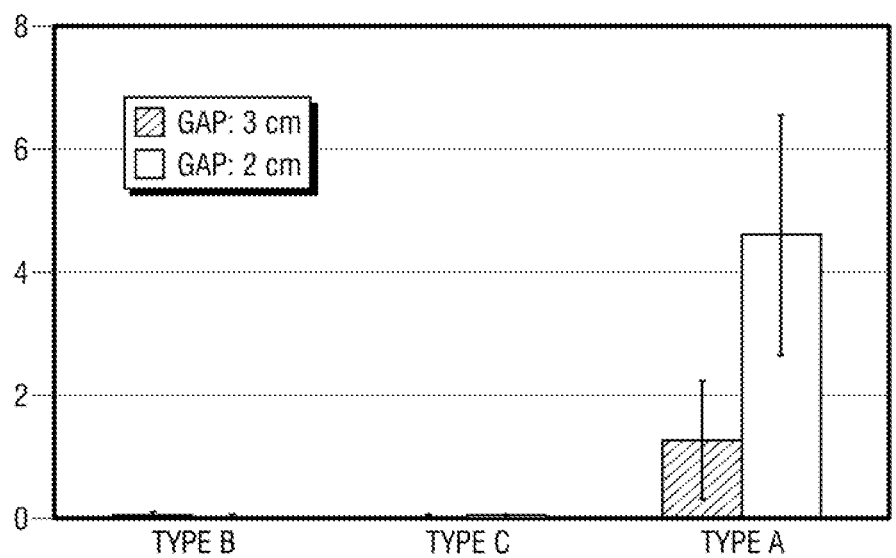
FIG. 12 is a graph showing the percentage of water lost during a water-displacement test.

The devices of Example 1 were subjected to this test, and the water loss percentage for each device at gaps of 2 cm and 3 cm are shown in FIG. 12. FIG. 12 shows that the device having a plug with an orifice, Type A, suffered significant water loss compared to the other devices that had orifice-free restraining plugs—the Type B and Type C devices.

The water loss of a number of other devices was also tested and compared with the water loss of devices similar to those in Example 1. Each device had an elastic body comprising a drug reservoir lumen and a retention frame lumen. The retention frame lumen of each device containing a nitinol wire retention frame, which kept the devices in the above-described "pretzel" retention shape. The other characteristics of the devices are explained in Table 1 below. The outer diameter of each restraining plug was about 5% larger than the inner diameter (ID) of the drug reservoir lumen.

TABLE 1

| | Drug Reservoir Lumen | | | |
|---|---|---|---|---|
| Device No. | ID (mm) | Orifice* (mm) | First End | Second End |
| 1 | 2.64 | N/A | Restraining Plug | Restraining Plug |
| 2 | 2.64 | N/A | Restraining Plug | Restraining Plug + Sealed with Silicone Adhesive |
| 3 | 2.64 | 0.050 | Restraining Plug + Sealed with Silicone Adhesive | Restraining Plug + Sealed with Silicone Adhesive |
| 4 | 2.64 | 0.075 | Restraining Plug + Sealed with Silicone Adhesive | Restraining Plug + Sealed with Silicone Adhesive |
| 5 | 2.64 | 0.125 | Restraining Plug + Sealed with Silicone Adhesive | Restraining Plug + Sealed with Silicone Adhesive |
| 6 | 2.64 | 0.150 | Restraining Plug + Sealed with Silicone Adhesive | Restraining Plug + Sealed with Silicone Adhesive |
| 7 | 2.64 | 0.150 | 6 Restraining Plugs + Sealed with Silicone Adhesive | 6 Restraining Plugs + Sealed with Silicone Adhesive |
| 8 | 1.52 | 0.150 | Restraining Plug + Sealed with Silicone Adhesive | Restraining Plug + Sealed with Silicone Adhesive |
| 9 | 2.16 | 0.150 | Restraining Plug + Sealed with Silicone Adhesive | Restraining Plug + Sealed with Silicone Adhesive |
| 10 | 2.64 | N/A | Plug having Orifice with 0.3 mm diameter | Restraining Plug + Sealed with Silicone Adhesive |
| 11 | 2.64 | N/A | Plug having orifice with 0.3 mm diameter | Restraining Plug + Sealed with Silicone Adhesive (so that about half of the drug reservoir lumen was filled with adhesive) |
| 12 | 2.16 | N/A | Restraining Plug | Restraining Plug |
| 13 | 2.64 | N/A | Plug having Orifice with 0.127 mm diameter | Restraining Plug + Sealed with Silicone Adhesive |

TABLE 1-continued

| | Drug Reservoir Lumen | | | |
|---|---|---|---|---|
| Device No. | ID (mm) | Orifice* (mm) | First End | Second End |
| 14 | 2.64 | N/A | Plug having Orifice with 0.203 mm diameter | Restraining Plug + Sealed with Silicone Adhesive |
| 15 | 2.64 | N/A | Plug having orifice with 0.127 mm diameter | Restraining Plug + Sealed with Silicone Adhesive (so that about half of the drug reservoir lumen was filled with adhesive) |
| 16 | 2.64 | N/A | Plug having orifice with 0.203 mm diameter | Restraining Plug + Sealed with Silicone Adhesive (so that about half of the drug reservoir lumen was filled with adhesive) |

*The orifice was located in the middle of the drug reservoir tube.

Devices 1, 2, and 12 were designed according to embodiments described herein. Both ends of devices 1, 2, and 12 were fitted with restraining plugs. In device 2, however, silicone adhesive was applied in the drug reservoir lumen after the restraining plug had been inserted in one end of the device, thereby sealing that end of the device. The restraining plug was inserted into the drug reservoir lumen only far enough to allow silicone adhesive to be applied in the drug reservoir lumen in an amount effective to seal the end of the device.

The same technique was used to seal both ends of devices 3-9. A restraining plug was inserted into each ends of the devices, and in each end silicone adhesive was applied to seal both ends of the devices. In devices 3-6, 8, and 9 a single restraining plug was inserted into each end of the devices. The restraining plugs were inserted far enough to allow the silicone adhesive to be applied in the drug reservoir lumen in an amount effective to seal both ends of the devices. In device 7, six restraining plugs were inserted into each end of the devices, the sixth being inserted only far enough to allow the silicone adhesive to be applied inside the drug reservoir lumen in an amount effective to seal both ends of the device.

Devices 10, 11, and 13-16 had one end in which silicone adhesive was applied in the drug reservoir lumen after the restraining plug had been inserted, thereby sealing that end of the device. In devices 10, 13, and 14 the restraining plug was inserted only far enough into the drug reservoir lumen to allow for the silicone adhesive to be applied behind it. In devices 11, 15, and 16, however, the restraining plug was positioned near the center of the device so that the silicone adhesive filled about half the volume of the drug reservoir lumen. The other ends of devices 10, 11, and 13-16 were fitted with a plug having an orifice with the diameters listed in the preceding table. The outer surface of the plug was sealed with silicone adhesive. The orifices present in the plugs allowed the contents of the drug reservoir lumen to be in fluid communication with the external environment.

Figure 13:
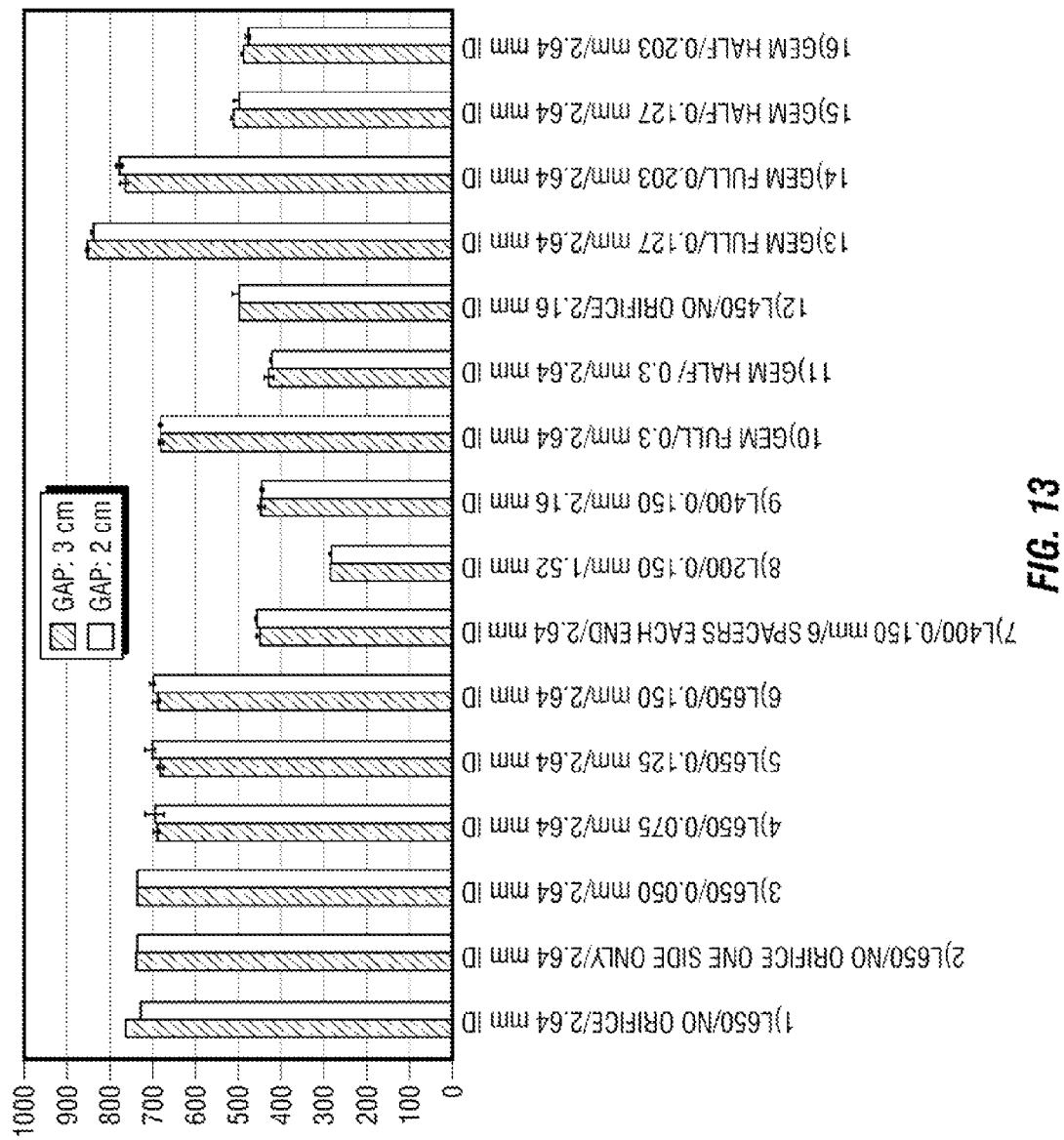
FIG. 13 is a graph showing the amount of water initially placed in the devices before the water-displacement tests.
Figure 14:
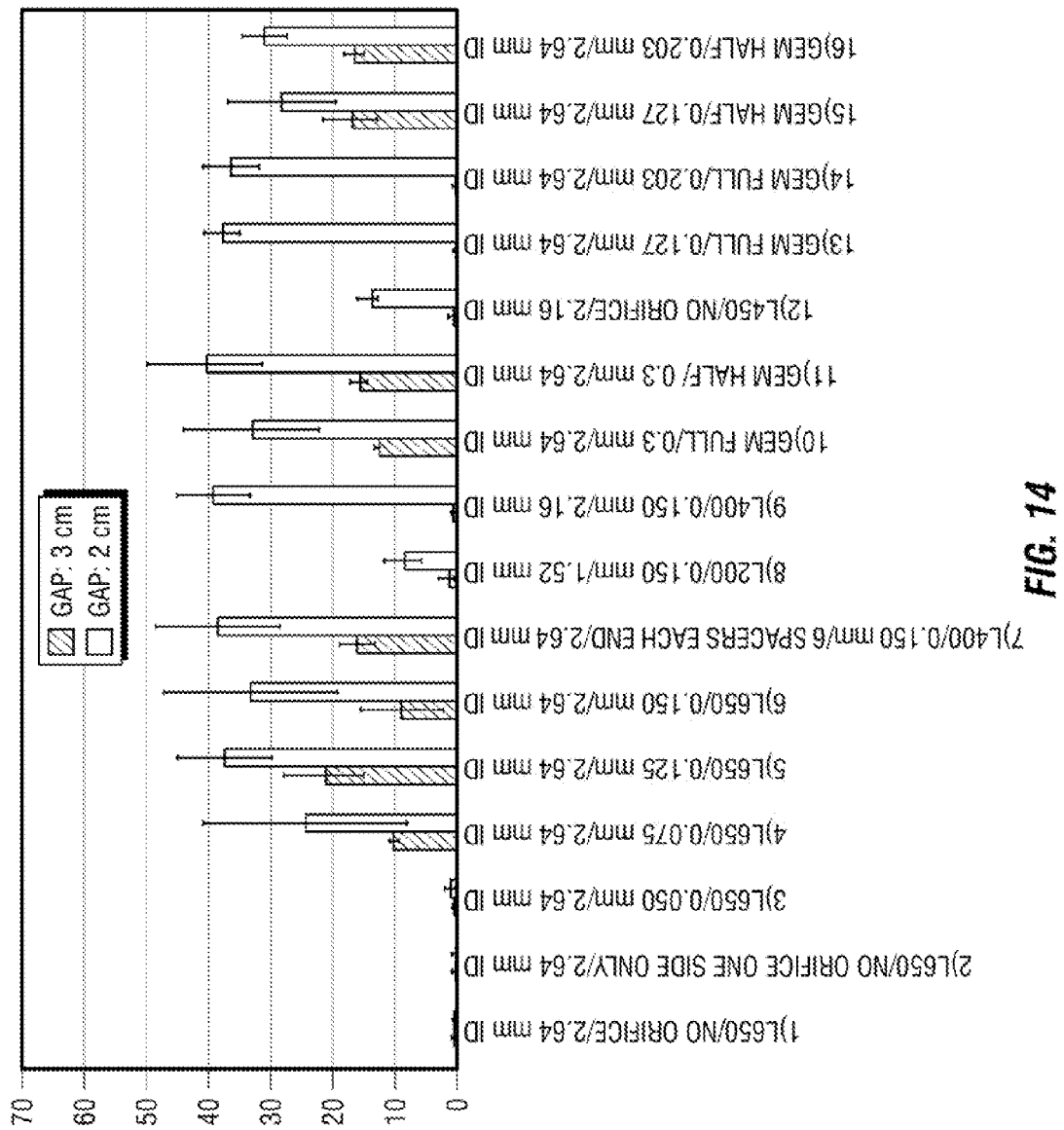
FIG. 14 is a graph showing the amount of water lost during the water-displacement test.
Figure 15:
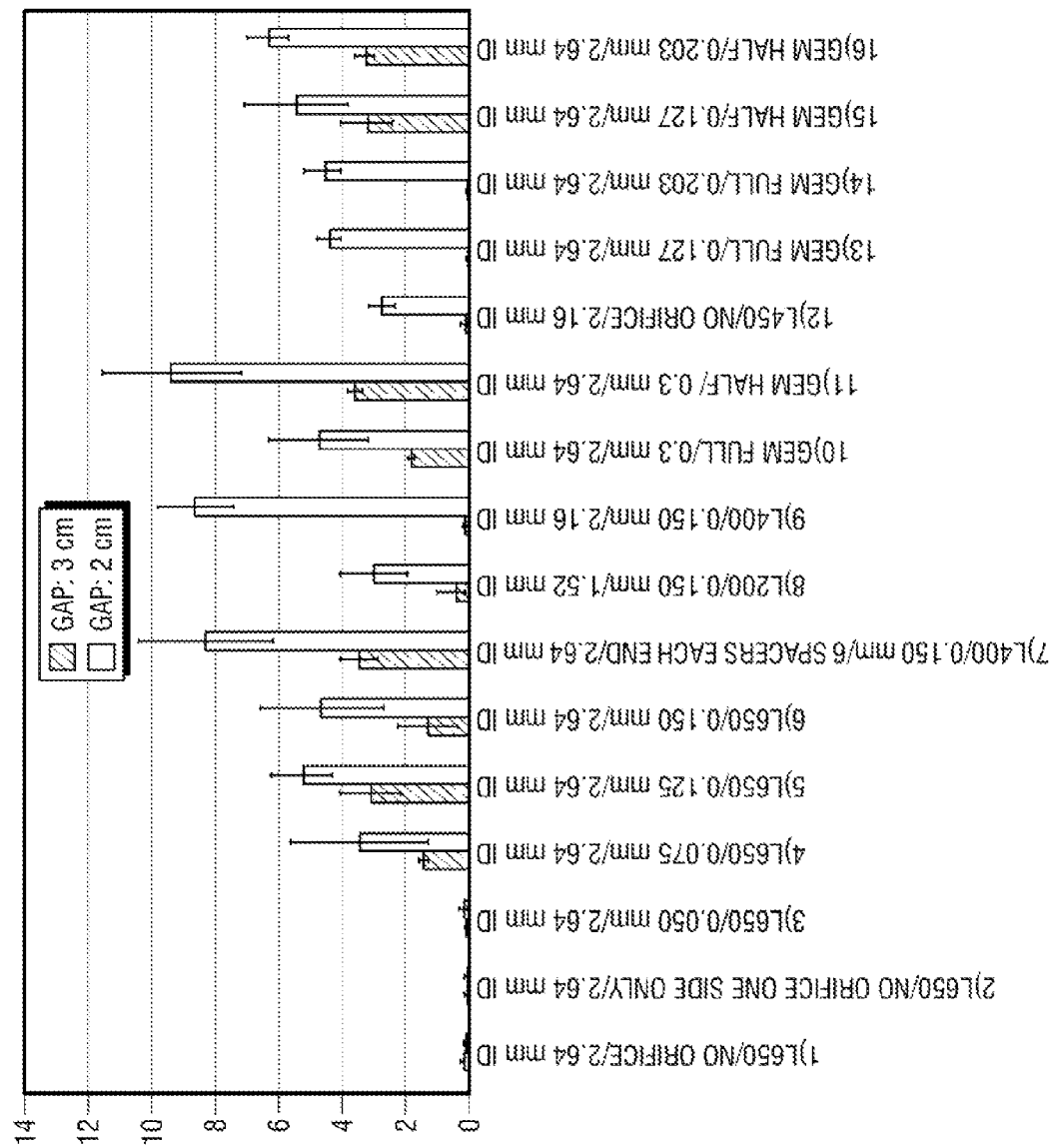
FIG. 15 is a graph showing the percentage of water lost during the water-displacement test.

The initial amount of water placed in each device is shown in FIG. 13. The amount of water inserted into each device depended, at least in part, on the internal diameter of the drug reservoir lumen and the volume of the drug reservoir lumen consumed by silicone adhesive (as in devices 11, 15, and 16) or restraining plugs (as in device 7). The amount of water lost and the percentage of water lost from each device as the devices were compressed to a gap of 2 cm and 3 cm are shown in FIGS. 14 and 15, respectively. These figures show that the devices embodied by the present disclosure—devices 1, 2, and 12—generally lost less water during compression than the other devices. Therefore, the orifice-free drug delivery devices were less likely to expel an unwanted amount of drug during compression.

Example 3—In Vitro Release

The in vitro drug release performance of several configurations of drug delivery devices was tested. None of the drug delivery devices of this example included apertures.

The drug delivery devices of this example were made using a dual-lumen silicone tube. One of the lumens was a retention frame lumen containing a retention frame. The retention frame was a 0.254 mm diameter wireform. The other lumen of the dual-lumen silicone tube was a drug reservoir lumen having an inner diameter of 2.16 mm. The drug reservoir lumens of the devices hosted LHM tablets (89.5% lidocaine hydrochloride monohydrate, 2.5% PVP, 8% PEG 8000). The lidocaine FBE mass was about 470 mg. The devices of this example were not exposed to gamma irradiation.

The devices made and tested in this example are summarized in Table 2, which explain whether the ends of the devices included a restraining plug or a seal. In the tables, "CRP" is a cylindrical restraining plug, "OD" indicates outer diameter, and "L" is length. An "PTA/seal" is a room-temperature vulcanization seal.

TABLE 2

| Device No. | End 1 | End 2 | Note |
|---|---|---|---|
| 1 | CRP 2.27 mm OD, 5 mm L (friction fit) | RTV seal | 5% oversized CRP |
| 2 | CRP 2.64 mm OD, 5 mm L (friction fit) | RTV seal | 22% oversized CRP |
| 3 | CRP 2.77 mm OD, 5 mm L (friction fit) | RTV seal | 28% oversized CRP |
| 4 | CRP 2.27 mm OD, 3 mm L (friction fit) | RTV seal | 5% oversized CRP |
| 5 | CRP 2.64 mm OD, 3 mm L (friction fit) | RTV seal | 22% oversized CRP |
| 6 | CRP 2.77 mm OD, 3 mm L (friction fit) | RTV seal | 28% oversized CRP |
| 7 | CRP 2.64 mm OD, 5 mm L (friction fit) 0.3 mm orifice in CRP | RTV seal | 22% oversized CRP |

TABLE 2-continued

| Device No. | End 1 | End 2 | Note |
|---|---|---|---|
| 8 | CRP 2.27 mm OD, 5 mm L (friction fit) | Same as End 1 | 5% oversized CRPs 150 μm laser-drilled orifice in middle of silicone tube |
| 9 | RTV seal | RTV seal | 150 μm laser-drilled orifice in middle of silicone tube |
| 10 | CRP 2.27 mm OD, 5 mm L (friction fit) | RTV seal | Cylindrical spacer also placed in middle of drug core. |
| 11 | CRP 2.27 mm OD, 5 mm L (friction fit) | Same as End 1 | 5% oversized CRP |
| 12 | CRP 2.24 mm OD, 5 mm L (friction fit) | RTV seal | 4% oversized CRP |
| 13 | Sapphire Ball 2.38 mm OD (friction fit) | RTV seal | 10% oversized ball |
| 14 | Sapphire Ball 2.50 mm OD (friction fit) | RTV seal | 16% oversized ball |
| 15 | CRP 2.49 mm OD, 5 mm L (friction fit) | RTV seal | 15% oversized CRP |
| 16 | CRP 2.24 mm OD, 3 mm L (friction fit) | RTV seal | 4% oversized CRP |
| 17 | Sapphire Ball 2.78 mm OD (friction fit) | RTV seal | 29% oversized ball |
| 18 | Sapphire Ball 3.00 mm OD (friction fit) | RTV seal | 39% oversized ball |
| 19 | CRP 2.49 mm OD, 3 mm L (friction fit) | RTV seal | 15% oversized CRP |
| 20 | CRP 2.64 mm OD, 5 mm L (friction fit) | Same as End 1 | 22% oversized CRP 150 μm laser-drilled orifice in middle of silicone tube |
| 21 | CRP 2.77 mm OD, 5 mm L (friction fit) | Same as End 1 | 28% oversized CRP 150 μm laser-drilled orifice in middle of silicone tube |
| 22 | CRP 2.27 mm OD, 3 mm L (friction fit) | Same as End 1 | 5% oversized CRP |
| 23 | CRP 2.27 mm OD, 5 mm L (friction fit) | Same as End 1 | 5% oversized CRP |
| 24 | RTV seal | RTV seal | Both ends sealed |

The in vitro drug release performance of the 24 configurations of the drug delivery devices was measured by placing the devices in 300 mL of deionized water at 37° C. A daily time point was then collected by taking a 1 mL sample of water and replacing it with 1 mL of deionized water. The sample size tested for each configuration was 3.

It was generally observed that as the oversize percentage of the cylindrical restraining plugs decreased, the percentage of drug released from the devices increased and became more consistent. For example, the devices of configurations 16 and 12 released the drug substantially consistently over the 14 days test period, and, at the end of the test period, the devices of both configurations released about 60% of the drug. In contrast, the devices of configurations 6 and 3 release the drug in a more inconsistent manner over the 14 day test period. At the end of the test period, the 3 devices of configuration 6 released from about 45% to about 64% of the drug, and the 3 devices of configuration 3 released from about 43% to about 48% of the drug. Interestingly, a restraining plug was pushed out of 2 of the 3 devices of configuration 19 and 1 of the 3 devices of configuration 15 at day 2 of the 14 day test period. Configurations 19 and 15 included 15% oversized cylindrical restraining plugs, and these were the only cylindrical restraining plugs that were pushed out of the devices during the tests of this example.

Figure 16:
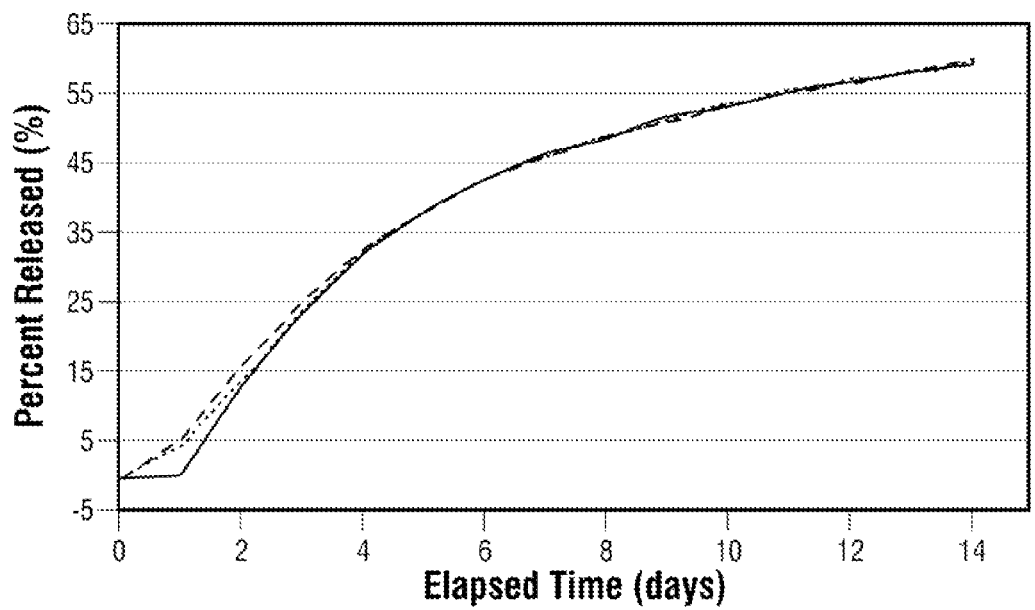
FIG. 16 is a graph showing the percentage of drug released in vitro by devices including a 5% oversized cylindrical restraining plug, according to one embodiment.

Regarding the percentage of drug released over the 14 day test period, it was generally observed that the devices having a single restraining plug and a sealed end performed similarly to those having two restraining plugs, i.e., one in each end of the device. For example, FIG. 16 depicts the percentage of drug released by three devices of configuration 4. The three devices of configuration 4 consistently released nearly identical percentages of drug, especially from days 4 through 14 of the test period. When the test period ended after 14 days, each of the 3 devices of configuration 4 had released about 60% of the drug.

Figure 17:
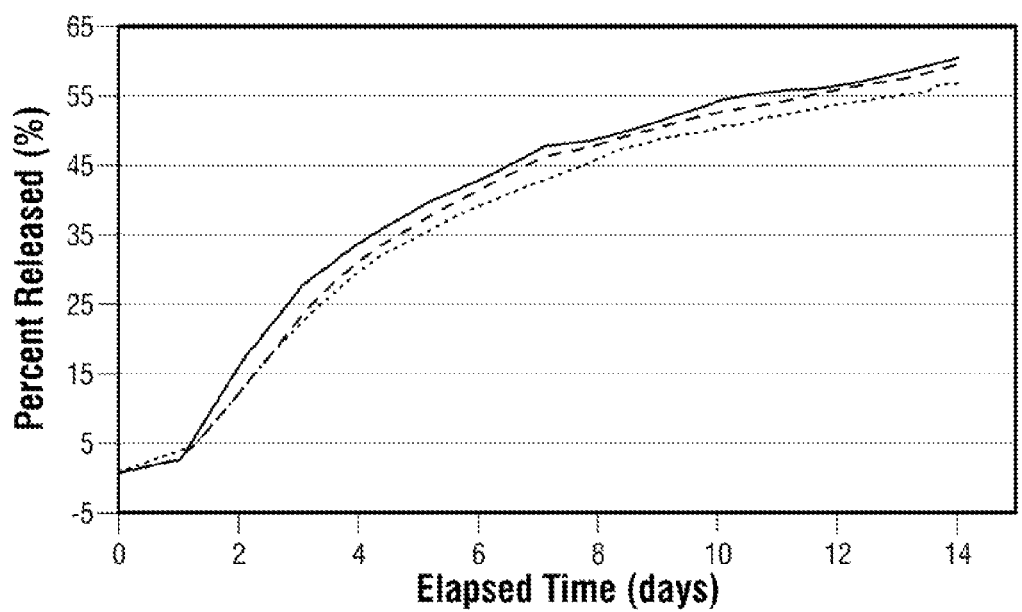
FIG. 17 is a graph showing the percentage of drug released in vitro by devices including two 5% oversized cylindrical restraining plugs, according to one embodiment.

Three devices of configuration 22 performed similarly to those of configuration 4 (shown in FIG. 16) despite the fact that the devices of configuration 22 included a restraining plug in both ends of the devices. The performance of the three devices of configuration 22 is shown in FIG. 17. FIG. 17 shows that the devices of configuration 22 performed similarly, but not as consistency as those of configuration 4. This indicated by the fact that the three devices of configuration 22 released from about 57% to about 61% percent of the drug at the conclusion of the 14 day test period. In contrast, each of the devices of configuration 4 released about 60% of the drug at the conclusion of the 14 day test period, as shown in FIG. 16.

It was also generally observed that the Sapphire balls were more likely to be pushed out of the devices that the cylindrical restraining plugs. For example, 3 devices of configuration 13 were tested, and the Sapphire balls of each of the 3 devices were pushed out on day 2 of the 14 day test period.

Overall, the data indicated that the orifice-free devices can release lidocaine predictably and consistently. The lidocaine release can be driven by the swelling of the silicone tube due to osmotic pressure. The data also indicated that the degree of interference fit between the spacer and the tube can affect in vitro release.

Example 4—Effect of Gamma Irradiation

The effect of gamma irradiation (25 kGy) on drug release from a drug delivery device was tested.

Four test groups of devices were developed for this example. Each device in this example was made from a dual-lumen silicone tube (50 Shore A durometer silicone). One of the lumens was a retention frame lumen that housed a bi-oval shaped retention frame, and the other lumen was a drug reservoir lumen having an inner diameter of 2.16 mm, and wall thickness of 0.20 mm. The composition of the drug tablets disposed in the silicone tube was 89.5% lidocaine hydrochloride, 2.5% of PVP, and 8% of PEG 8000. The tablet mass loaded into each device was about 650 mg, and the combined tablet length was about 15.7 cm.

One end of each device was sealed, and a restraining plug was inserted into the other end of each device. The devices of this example included restraining plugs made from one of two different materials: silicone and ethylene vinyl acetate (EVA) copolymer. The silicone restraining plugs (80 Shore A durometer silicone) had an outer diameter of 2.27 mm, and a length of 5 mm. The EVA plugs had an outer diameter of 2.34 mm, a length of 5 mm, and was made from support beading (Elvax® 760, EVA copolymer) (FBK medical tubing, Stirling, N.J.).

Both ends of the substantially cylindrical plugs were flat, and in view of the above-described dimensions, the silicone plugs and EVA plugs were oversized by 5% and 8%, respectively, compared to the 2.16 mm inner diameter of the silicone tube.

Gamma irradiation at 25 kGy was performed for the devices in groups 1 and 3 of the 4 test groups. The combinations are shown in Table 3 below.

TABLE 3

| Test Group | Restraining Plug Material | Gamma Irradiation (25 kGy) of Restraining Plug |
|---|---|---|
| 1 | Silicone | Yes |
| 2 | Silicone | No |
| 3 | EVA | Yes |
| 4 | EVA | No |

Figure 18:
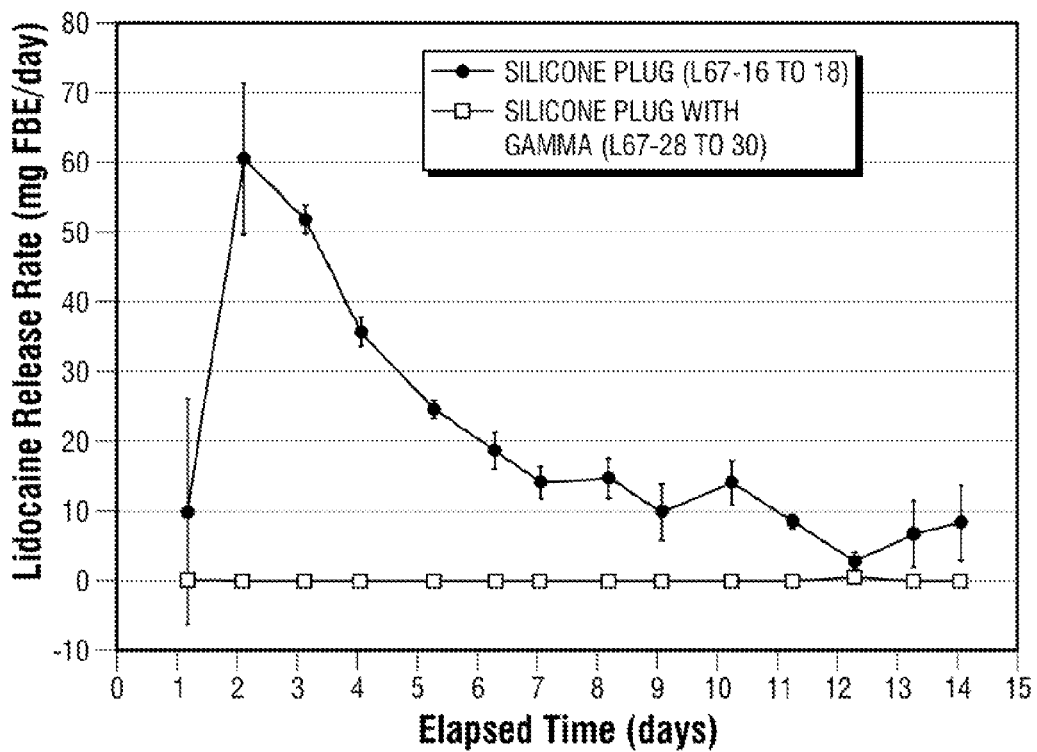
FIG. 18 is a graph showing lidocaine release rate in vitro for devices having 5% oversized silicone restraining plugs, according to one embodiment.
Figure 19:
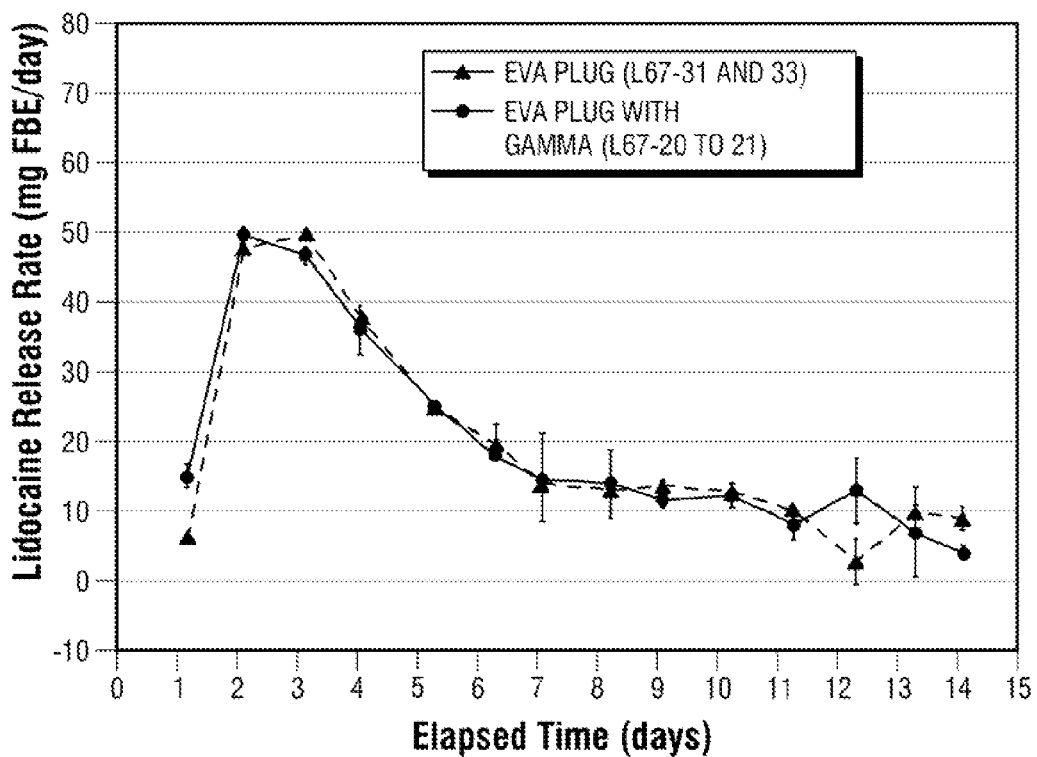
FIG. 19 is a graph showing lidocaine release rate in vitro for devices having 8% oversized ethylene vinyl acetate restraining plugs, according to one embodiment.

The in vitro release of the drug was tested in deionized water at 37° C. FIG. 18 depicts the daily lidocaine release rate for test groups 1 and 2, which contained the 5% oversized silicone restraining plugs. FIG. 19 depicts the daily lidocaine release rate for test groups 3 and 4, which contained the 8% oversized EVA restraining plugs. The sample size for each group in FIGS. 18 and 19 was 3. The errors bars in FIGS. 18 and 19 indicate standard deviation around the mean.

As shown in FIG. 18, the devices having the silicone restraining plugs exposed to 25 kGy gamma irradiation (test group 1) did not release any substantial amount of drug. In the devices of test group 1, some adherence occurred between the silicone restraining plugs and the silicone tube after 25 kGy gamma irradiation exposure. The adherence appeared to remain substantially intact as osmotic pressure increased in the silicone tube.

As shown in FIG. 19, there was no substantial difference in the drug release rates of test groups 3 and 4. Therefore, the exposure of the EVA restraining plugs to 25 kGy gamma irradiation did not substantially impact the rate of drug release. In each of test groups 3 and 4, however, an EVA restraining plug from one device of the three device sample was pushed out of the silicone tube. In test group 3, the EVA restraining plug was pushed out of the device at day 1 of the test, and in test group 4, the EVA restraining plug was pushed out of the device at day 4 of the test. Therefore, other EVA plug designs were tested, including the design of the following example.

Example 5—EVA Plug Design

Drug delivery devices having two configurations were tested to determine how restraining plugs of different sizes affected the release of lidocaine from the drug delivery devices.

As explained in Example 4, exposing the EVA restraining plug to 25 kGy gamma irradiation did not affect the lidocaine release rate, but the osmotic pressure pushed the EVA restraining plug out of 2 of the 6 units tested (1 unit from test group 3, and 1 unit from test group 4). Therefore, the substantially cylindrical EVA restraining plugs having flat ends of the previous example were replaced with EVA restraining plugs having the plug design shown in FIG. 20A.

Figure 20A:
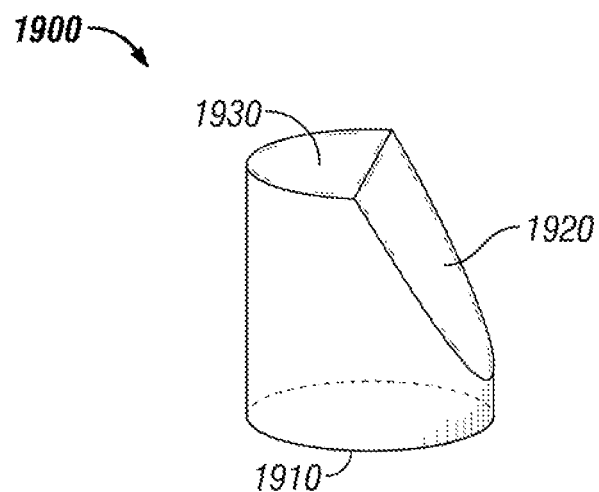
FIG. 20A is a perspective view of another embodiment of a restraining plug.
Figure 20B:
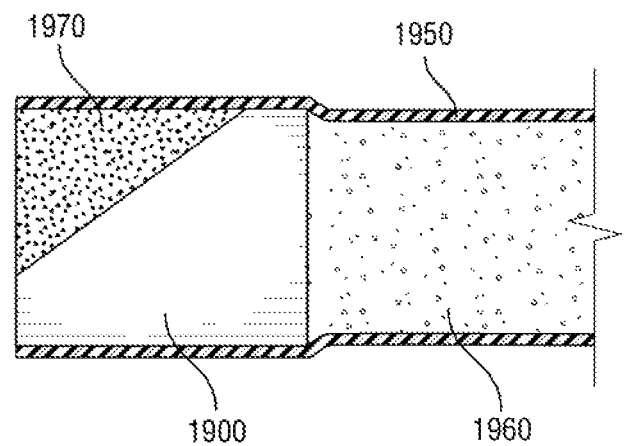
FIG. 20B is a cross-sectional view of the restraining plugs of FIG. 20A as inserted into an elastic portion of the body of one embodiment of a drug delivery device. Only a portion of the body is shown.

The restraining plug 1900 of FIG. 20A is a substantially cylindrical restraining plug having an angled portion 1920. The presence of the angled portion 1920 creates a restraining plug having a substantially semi-circular end 1930 and a substantially circular base 1910. The circular base 1910, in this particular example, was inserted into the silicone tube 1950 of the devices so that the circular base 1910 was in communication with the drug reservoir 1960 of the drug delivery device, as shown in FIG. 20B. An adhesive 1970 was placed in the void space created by the angled portion 1920 of the restraining plug 1900. In other embodiments, however, the semi-circular end 1930 can be inserted into the silicone tube of the devices so that the semi-circular end 1930 is in communication with the interior of the drug delivery device.

In each drug delivery device of this example, the devices were made from a dual-lumen silicone tube (50 Shore A durometer). One lumen was a retention frame lumen that held bi-oval shaped retention frame, and the other lumen was the drug reservoir lumen. The drug reservoir lumen had an inner diameter of 2.16 mm and a wall thickness of 0.20 mm. Each device was loaded with drug tablets of the following composition: 89.5% LHM, 2.5% of PVP, and 8% of PEG 8000. The tablet mass loaded into each device was about 650 mg, and the combined tablet length was about 15.4 cm.

In the first configuration, both ends of the drug reservoir lumen of the silicone tube were sealed, and the drug reservoir lumen of the silicone tube had a laser-drilled aperture having a diameter of 0.15 mm. The aperture was laser-drilled substantially in the middle of the device, i.e., substantially equidistant between the ends.

In the second configuration, the drug reservoir lumen did not have an aperture, and only one end of the drug reservoir lumen was sealed. The other end of the drug reservoir lumen hosted a restraining plug having a length of about 5 mm. Three devices of the second configuration were made and tested.

The three devices of the second configuration included restraining plugs having diameters of 2.18 mm, 2.21 mm, and 2.34 mm, respectively, so the restraining plugs of the three devices were oversized by 1%, 2%, and 8%, respectively, in view of the 2.16 mm inner diameter of the drug reservoir lumen of the silicone tube.

The restraining plugs were made from support beading (FBK medical tubing, Stirling, N.J.) of Elvax® 760, EVA copolymer. The restraining plugs were placed into the ends of the drug reservoir lumens. The substantially circular ends of the restraining plugs were the first portions of the restraining plugs placed into the drug reservoir lumens. As a result, the void spaces created by the angled surfaces of the restraining plugs were accessible from the ends of the devices after the restraining plugs were inserted. The void spaces were filled with silicone adhesive, as shown in FIG. 20B. The silicone adhesive, in this example, served as a stopper to prevent the detachment and expulsion of the restraining plugs as osmotic pressure increased in the devices.

Figure 21:
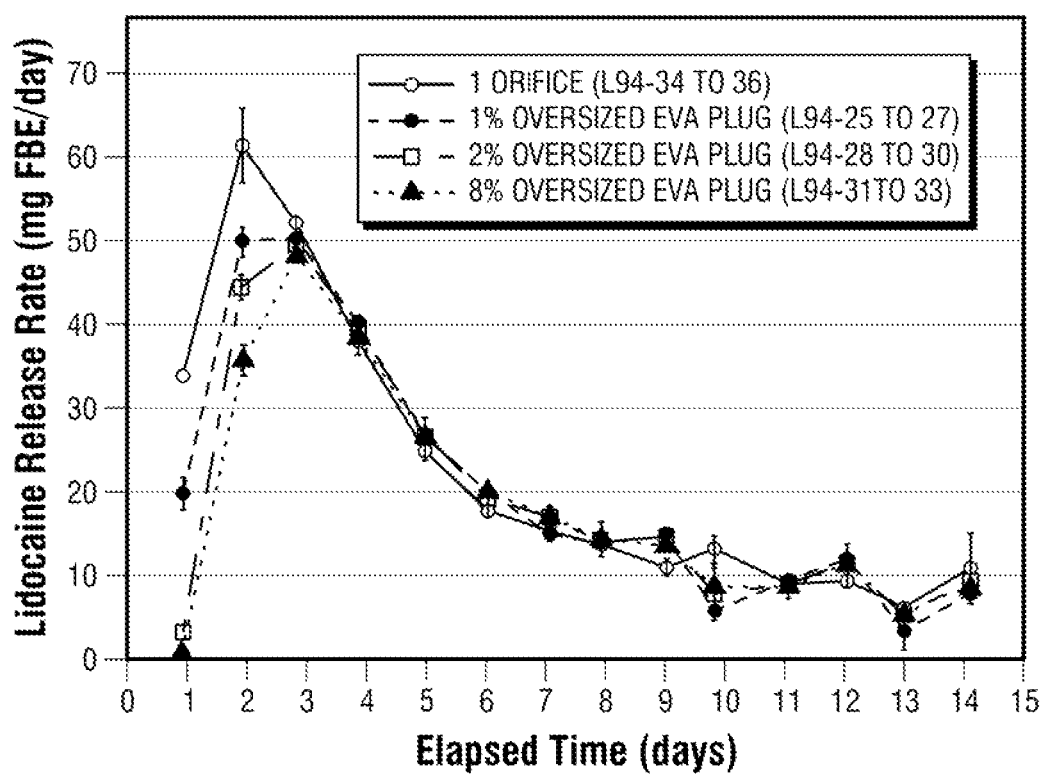
FIG. 21 is a graph showing lidocaine release rate in vitro from of various configurations of drug delivery devices, according to embodiments described herein.

For each device, the in vitro release of the drug was tested in deionized water at 37° C. The four previously-described device configurations were tested, and the sample size was three per configuration. FIG. 21 shows the results of the drug release experiments, and the errors bars indicate standard deviation around the mean. During the 14 day test, none of the restraining plugs was detached or pushed out of the devices.

Prior to day 3 of the test, as shown in FIG. 21, the drug delivery device having an aperture and the device having a 1% oversized restraining plug release lidocaine at a higher rate than the devices having 2% and 8% oversized restraining plugs. At or near day 3 of the test, the release rates of drug from each of the drug delivery devices, regardless of configuration, became substantially similar, and remained so throughout the remainder of the 14 day period.

Modifications and variations of the methods and devices described herein will be obvious to those skilled in the art from the foregoing detailed description. Such modifications and variations are intended to come within the scope of the appended claims.

I claim:

1. A drug delivery device comprising:
   a body having at least one water permeable wall bounding a reservoir defined within the body, wherein the body comprises an elastic portion;
   a drug formulation which comprises a drug, the drug formulation being disposed within the reservoir; and
   at least one restraining plug closing off an opening of the body, the opening being in fluid communication with the reservoir,
   wherein the at least one restraining plug contacts the elastic portion of the body and controls release of the drug from the device by the transient formation of one or more microchannels between the elastic portion of the body and the at least one restraining plug, and
   wherein the one or more microchannels are not preformed orifices.

2. The drug delivery device of claim 1, wherein:
   the at least one restraining plug has an outer diameter,
   the elastic portion of the body defines an opening having an inner diameter, and
   wherein the outer diameter of the restraining plug exceeds the inner diameter of the elastic portion of the body by at least 3%.

3. The drug delivery device of claim 2, wherein the outer diameter of the restraining plug exceeds the inner diameter of the elastic portion of the body by at least 5%.

4. The drug delivery device of claim 2, wherein the outer diameter of the restraining plug exceeds the inner diameter of the elastic portion of the body by at least 10%.

5. The drug delivery device of claim 2, wherein the outer diameter of the restraining plug exceeds the inner diameter of the elastic portion of the body by at least 15%.

6. The drug delivery device of claim 2, wherein the outer diameter of the restraining plug exceeds the inner diameter of the elastic portion of the body by at least 20%.

7. The drug delivery device of claim 2, wherein the outer diameter of the restraining plug exceeds the inner diameter of the elastic portion of the body by at least 25%.

8. The drug delivery device of claim 1, wherein the body further comprises an inelastic portion.

9. The drug delivery device of claim 1, wherein the at least one restraining plug is secured within the opening in the elastic portion of the body with an adhesive.

10. The drug delivery device of claim 1, wherein the drug formulation is in a solid form.

11. The drug delivery device of claim 1, wherein the drug comprises lidocaine or another anesthetic agent.

12. The drug delivery device of claim 1, further comprising an osmotic agent.

13. The drug delivery device of claim 12, wherein the osmotic agent is a component of the drug formulation.

14. The drug delivery device of claim 1, wherein the at least one restraining plug is substantially cylindrical.

15. The drug delivery device of claim 1, wherein the at least one restraining plug comprises a wedged, tapered, angled, or rounded surface.

16. The drug delivery device of claim 1, wherein the Shore durometer of the elastic portion of the body is from about 40 A to about 60 A, and the Shore durometer of the at least one restraining plug is from about 70 A to about 100 A.

17. The drug delivery device of claim 1, wherein the Shore durometer of the elastic portion of the body is from about 45 A to about 55 A, and the Shore durometer of the at least one restraining plug is from about 75 A to about 85 A.

18. The drug delivery device of claim 1, wherein the Shore durometer of the elastic portion of the body is about 50 A, and the Shore durometer of the at least one restraining plug is about 80 A.

19. The drug delivery device of claim 1, wherein the device is elastically deformable between a relatively straightened shape suitable for insertion through a lumen into a body cavity of a patient and a retention shape suited to retain the device within the body cavity.

20. A method of administering a drug to a patient, comprising:
   inserting the drug delivery device of claim 1 into a lumen or body cavity of a patient; and
   permitting water influx into the reservoir to develop a hydrostatic pressure in the reservoir effective to form one or more microchannels between the elastic portion of the body and the at least one restraining plug, thereby causing the drug to flow from the reservoir, through the microchannels, and out of the device and into the lumen or body cavity.

21. The method of claim 20, wherein the body cavity is the bladder of the patient.

22. A drug delivery device comprising:
   a body having at least one water-permeable wall bounding a reservoir defined within the body, wherein the at least one water-permeable wall comprises an elastic portion;
   a solid drug formulation which comprises a drug, the drug formulation being disposed within the reservoir; and
   at least one restraining plug closing off an opening of the body, the opening being in fluid communication with the reservoir,
   wherein the at least one restraining plug contacts the elastic portion of the at least one water-permeable wall and controls release of the drug from the device by the transient formation of one or more microchannels between the elastic portion of the at least one water-permeable wall and the at least one restraining plug, and
   wherein the one or more microchannels are not preformed orifices.

* * * * *